(12) United States Patent
Leung et al.

(10) Patent No.: US 7,135,314 B1
(45) Date of Patent: Nov. 14, 2006

(54) HUMAN PHOSPHATIDIC ACID PHOSPHATASE

(75) Inventors: David W. Leung, Mercer Island, WA (US); Christopher K. Tompkins, Bothell, WA (US)

(73) Assignee: Cell Therapeutics, Inc., Seattle, WA (US)

( * ) Notice: Subject to any disclaimer, the term of this patent is extended or adjusted under 35 U.S.C. 154(b) by 0 days.

(21) Appl. No.: 08/842,827

(22) Filed: Apr. 17, 1997

(51) Int. Cl.
*C12N 9/16* (2006.01)
*C12N 15/55* (2006.01)
*C12P 7/64* (2006.01)

(52) U.S. Cl. ........................ 435/134; 435/196; 435/41; 435/128; 435/135; 435/147; 435/262; 536/23.2

(58) Field of Classification Search ................ 435/196, 435/41, 128, 134, 135, 147, 262; 536/23.2
See application file for complete search history.

(56) References Cited

OTHER PUBLICATIONS

E. Boder et al., "Identification of Type-2 Phosphatidic Acid Phosphohydrolase (PAPH-2) in Neutrophil Plasma Membranes", Cellular Signalling 6(8): 933-941, 1994.*
GENBANK entry U79294, Jan. 1997.*
GENBANK entry AA040858, Aug. 1996.*
GENBANK entry W04968, Apr. 1996.*
GENBANK entry H68363, Oct. 1995.*
Brindley, D.N. et al., "Phosphatidate phosphohydrolase and signal transduction," *Chemistry and Physics of Lipids*, vol. 80, pp. 45-57 (1996).
Kent, C., "Eukaryotic Phospholipid Biosynthesis," *Annu. Rev. Biochem*, vol. 64, pp. 316-343 (1995).
Abraham, E. et al., "Phosphatidic Acid Signaling Mediates Lung Cytokine Expression and Lung Inflammatory Injury After Hemorrhage in Mice," *J. Exp. Med.*, vol. 181, pp. 569-575 (1995).

Dillon, D.A. et al., "The *Escherichia coli* pgpB Gene Encodes for a Diacylglycerol Pyrophosphate Phosphatase Activity," *J. Biol. Chem.*, vol. 271, No. 48, pp. 30548-30553 (1996).
Rice, G.C. et al., "Protection from endotoxic shock in mice by pharmacologic inhibition of phosphatidic acid," *Proc. Natl. Acad. Sci. USA*, vol. 91, pp. 3857-3861 (1994).
Bursten, S. et al., "Potential Role for Phosphatidic Acid in Mediating the Inflammatory Responses to TNFα and IL-1β," *Circulatory Shock*, vol. 44, pp. 14-29 (1994).
Kai, M. et al., "Identification and cDNA Cloning of 35-kDa Phosphatidic Acid Phosphatase (Type 2) Bound to Plasma Membranes," *J. Biol. Chem.*, vol. 271, No. 31, pp. 18931-18938 (1996).
Leung, D.W. et al., "CT-2576, an inhibitor of phospholipid signaling, suppresses constitutive and induced expression of human immunodeficiency virus," *Proc. Natl. Acad. Sci. USA*, vol. 92, pp. 4813-4817 (1995).
Barila, D. et al., "The Dri 42 Gene, Whose Expression Is Up-regulated during Epithelial Differentiation, Encodes a Novel Endoplasmic Reticulum Resident Transmembrane Protein," *J. Biol. Chem.*, vol. 271, No. 47, pp. 29928-29936 (1996).
Shen, H. et al., "The CDS1 Gene Encoding CDP-diacylglycerol Synthase In *Saccharomyces cerevisiae* Is Essential for Cell Growth," *J. Biol. Chem.*, vol. 271, No. 2, pp. 789-795 (1996).
English, D. et al., "Messenger functions of phosphatidic acid," *Chemistry and Physics of Lipids*, vol. 80, pp. 117-132 (1996).
Levitzki, A., "Targeting signal transduction for disease therapy," *Current Opinion on Cell Biology*, vol. 8, pp. 239-244 (1996).
GenBank human cDNA clone N75714, Jan. 1997.
GenBank human cDNA clone W70040, Oct. 1996.
GenBank human cDNA clone H17855, Jun. 1995.

* cited by examiner

*Primary Examiner*—Rebecca E. Prouty
(74) *Attorney, Agent, or Firm*—Foley & Lardner LLP

(57) ABSTRACT

This invention relates to a biotechnology invention concerning human phosphatidic acid phosphatase. More particularly, this invention relates to three variants of human phosphatidic acid phosphatase namely PAP-α(1 and 2), PAP-β and PAP-γ and uses thereof.

8 Claims, 9 Drawing Sheets

Fig. 1

```
CCTGTGGGAGAGAGCGCCGGGATCCGGACGGGGTAGCAACCGGGGCAGGCCGTGCCGGCTGA    62
GGAGGTCCTGAGGCTACAGAGCTGCCGCGGCTGGCACACGAGCGCCTCGGCACTAACCGA     122
GTGTTCGCGGGGGCTGTGAGGGGAGGGCCCCGGGCGCCATTGCTGGCGGTGGGAGCGCCG     182
CCCGGTCTCAGCCCGCCCTCGGCTGCTCTCCTCCTCCGGCTGGGAGGGGCCGTATCTCGG     242
GGCCGTCGCCAGCCCCGGCCCGGGCTCGATAATCAAGGGCCTCGGCCGTCGTCCCGCACC     302
TCATTCCATCGCCCTTGCCGGGCAGCCCGGGCAGAGACC ATG TTT GAC AAG ACG     356
                                        Met Phe Asp Lys Thr
                                                          5
CGG CTG CCG TAC GTG GCC CTC GAT GTG CTC TGC GTG TTG CTG GCT     401
Arg Leu Pro Tyr Val Ala Leu Asp Val Leu Cys Val Leu Leu Ala
            10                  15                      20
GGA TTG CCT TTT GCA ATT CTT ACT TCA AGG CAT ACC CCC TTC CAA     446
Gly Leu Pro Phe Ala Ile Leu Thr Ser Arg His Thr Pro Phe Gln
            25                  30                      35
CGA GGA GTA TTC TGT AAT GAT GAG TCC ATC AAG TAC CCT TAC AAA     491
Arg Gly Val Phe Cys Asn Asp Glu Ser Ile Lys Tyr Pro Tyr Lys
            40                  45                      50
GAA GAC ACC ATA CCT TAT GCG TTA TTA GGT GGA ATA ATC ATT CCA     536
Glu Asp Thr Ile Pro Tyr Ala Leu Leu Gly Gly Ile Ile Ile Pro
            55                  60                      65
TTC AGT ATT ATC GTT ATT ATT CTT GGA GAA ACC CTG TCT GTT TAC     581
Phe Ser Ile Ile Val Ile Ile Leu Gly Glu Thr Leu Ser Val Tyr
            70                  75                      80
TGT AAC CTT TTG CAC TCA AAT TCC TTT ATC AGG AAT AAC TAC ATA     626
Cys Asn Leu Leu His Ser Asn Ser Phe Ile Arg Asn Asn Tyr Ile
            85                  90                      95
GCC ACT ATT TAC AAA GCC ATT GGA ACC TTT TTA TTT GGT GCA GCT     671
Ala Thr Ile Tyr Lys Ala Ile Gly Thr Phe Leu Phe Gly Ala Ala
            100                 105                     110
GCT AGT CAG TCC CTG ACT GAC ATT GCC AAG TAT TCA ATA GGC AGA     716
Ala Ser Gln Ser Leu Thr Asp Ile Ala Lys Tyr Ser Ile Gly Arg
            115                 120                     125
CTG CGG CCT CAC TTC TTG GAT GTT TGT GAT CCA GAT TGG TCA AAA     761
Leu Arg Pro His Phe Leu Asp Val Cys Asp Pro Asp Trp Ser Lys
            130                 135                     140
ATC AAC TGC AGC GAT GGT TAC ATT GAA TAC TAC ATA TGT CGA GGG     806
Ile Asn Cys Ser Asp Gly Tyr Ile Glu Tyr Tyr Ile Cys Arg Gly
            145                 150                     155
AAT GCA GAA AGA GTT AAG GAA GGC AGG TTG TCC TTC TAT TCA GGC     851
Asn Ala Glu Arg Val Lys Glu Gly Arg Leu Ser Phe Tyr Ser Gly
            160                 165                     170
CAC TCT TCG TTT TCC ATG TAC TGC ATG CTG TTT GTG GCA CTT TAT     896
His Ser Ser Phe Ser Met Tyr Cys Met Leu Phe Val Ala Leu Tyr
            175                 180                     185
CTT CAA GCC AGG ATG AAG GGA GAC TGG GCA AGA CTC TTA CGC CCC     941
Leu Gln Ala Arg Met Lys Gly Asp Trp Ala Arg Leu Leu Arg Pro
            190                 195                     200
ACA CTG CAA TTT GGT CTT GTT GCC GTA TCC ATT TAT GTG GGC CTT     986
Thr Leu Gln Phe Gly Leu Val Ala Val Ser Ile Tyr Val Gly Leu
            205                 210                     215
TCT CGA GTT TCT GAT TAT AAA CAC CAC TGG AGC GAT GTG TTG ACT     1031
Ser Arg Val Ser Asp Tyr Lys His His Trp Ser Asp Val Leu Thr
            220                 225                     230
GGA CTC ATT CAG GGA GCT CTG GTT GCA ATA TTA GTT GCT GTA TAT     1076
Gly Leu Ile Gln Gly Ala Leu Val Ala Ile Leu Val Ala Val Tyr
            235                 240                     245
GTA TCG GAT TTC TTC AAA GAA AGA ACT TCT TTT AAA GAA AGA AAA     1121
Val Ser Asp Phe Phe Lys Glu Arg Thr Ser Phe Lys Glu Arg Lys
            250                 255                     260
GAG GAG GAC TCT CAT ACA ACT CTG CAT GAA ACA CCA ACA ACT GGG     1166
Glu Glu Asp Ser His Thr Thr Leu His Glu Thr Pro Thr Thr Gly
            265                 270                     275
AAT CAC TAT CCG AGC AAT CAC CAG CCT TGA AAG GCAGCAGGGTGCCCAG    1215
Asn His Tyr Pro Ser Asn His Gln Pro ***
            280
GTGAAGCTGGCCTGTTTTCTAAAGGAAAATGATTGCCACAAGGCAAGAGGATGCATCTTT    1275
CTTCCTGGTGTACAAGCCTTTAAAGACTTCTGCTGCTGATATGCCTCTTGGATGCACACT    1335
TTGTGTGTACATAGTTACCTTTAACTCAGTGGTTATCTAATAGCTCTAAACTCATTAAAA    1395
AAACTCCAAGCCTTCCACCAAAACAGTGCCCCACCTGTATACATTTTTATTAAAAAAATG    1455
TAATGCTTATGTATAAACATGTATGTAATATGCTTTCTATGAATGATGTTTGATTTAAAT    1515
ATAATACATATTAAAATGTATGGGAGAACCAAAAAAAAAAAAAAAAAAA             1563
```

Fig. 2

```
CCTGTGGGAGAGAGCGCCGGGATCCGGACGGGGTAGCAACCGGGGCAGGCCGTGCCGGCTGA    62
GGAGGTCCTGAGGCTACAGAGCTGCCGCGGCTGGCACACGAGCGCCTCGGCACTAACCGA     122
GTGTTCGCGGGGGCTGTGAGGGGAGGGCCCCGGGCGCCATTGCTGGCGGTGGGAGCGCCG     182
CCCGGTCTCAGCCCGCCCTCGGCTGCTCTCCTCCTCCGGCTGGGAGGGGCCGTATCTCGG     242
GGCCGTCGCCAGCCCCGGCCCGGGCTCGATAATCAAGGGCCTCGGCCGTCGTCCCGCACC     302
TCATTCCATCGCCCTTGCCGGGCAGCCCGGGCAGAGACC ATG TTT GAC AAG ACG     356
                                        Met Phe Asp Lys Thr
                                                          5
CGG CTG CCG TAC GTG GCC CTC GAT GTG CTC TGC GTG TTG CTG GCT     401
Arg Leu Pro Tyr Val Ala Leu Asp Val Leu Cys Val Leu Leu Ala
             10                  15                      20
TCC ATG CCT ATG GCT GTT CTA AAA TTG GGC CAA ATA TAT CCA TTT     446
Ser Met Pro Met Ala Val Leu Lys Leu Gly Gln Ile Tyr Pro Phe
                     25                  30                  35
CAG AGA GGC TTT TTC TGT AAA GAC AAC AGC ATC AAC TAT CCG TAC     491
Gln Arg Gly Phe Phe Cys Lys Asp Asn Ser Ile Asn Tyr Pro Tyr
             40                  45                      50
CAT GAC AGT ACC GCC GCA TCC ACT GTC CTC ATC CTA GTG GGG GTT     536
His Asp Ser Thr Ala Ala Ser Thr Val Leu Ile Leu Val Gly Val
                 55                  60                      65
GGC TTG CCC GTT TCC TCT ATT ATT CTT GGA GAA ACC CTG TCT GTT     581
Gly Leu Pro Val Ser Ser Ile Ile Leu Gly Glu Thr Leu Ser Val
             70                  75                      80
TAC TGT AAC CTT TTG CAC TCA AAT TCC TTT ATC AGT AAT AAC TAC     626
Tyr Cys Asn Leu Leu His Ser Asn Ser Phe Ile Ser Asn Asn Tyr
                 85                  90                      95
ATA GCC ACT ATT TAC AAA GCC ATT GGA ACC TTT TTA TTT GGT GCA     671
Ile Ala Thr Ile Tyr Lys Ala Ile Gly Thr Phe Leu Phe Gly Ala
                100                 105                    110
GCT GCT AGT CAG TCC CTG ACT GAC ATT GCC AAG TAT TCA ATA GGC     716
Ala Ala Ser Gln Ser Leu Thr Asp Ile Ala Lys Tyr Ser Ile Gly
            115                 120                    125
AGA CTG CGG CCT CAC TTC TTG GAT GTT TGT GAT CCA GAT TGG TCA     761
Arg Leu Arg Pro His Phe Leu Asp Val Cys Asp Pro Asp Trp Ser
                130                 135                    140
AAA ATC AAC TGC AGC GAT GGT TAC ATT GAA TAC TAC ATA TGT CGA     806
Lys Ile Asn Cys Ser Asp Gly Tyr Ile Glu Tyr Tyr Ile Cys Arg
            145                 150                    155
GGG AAT GCA GAA AGA GTT AAG GAA GGC AGG TTG TCC TTC TAT TCA     851
Gly Asn Ala Glu Arg Val Lys Glu Gly Arg Leu Ser Phe Tyr Ser
                160                 165                    170
GGC CAC TCT TCG TTT TCC ATG TAC TGC ATG CTG TTT GTG GCA CTT     896
Gly His Ser Ser Phe Ser Met Tyr Cys Met Leu Phe Val Ala Leu
            175                 180                    185
TAT CTT CAA GCC AGG ATG AAG GGA GAC TGG GCA AGA CTC TTA CGC     941
Tyr Leu Gln Ala Arg Met Lys Gly Asp Trp Ala Arg Leu Leu Arg
                190                 195                    200
CCC ACA CTG CAA TTT GGT CTT GTT GCC GTA TCC ATT TAT GTG GGC     986
Pro Thr Leu Gln Phe Gly Leu Val Ala Val Ser Ile Tyr Val Gly
            205                 210                    215
CTT TCT CGA GTT TCT GAT TAT AAA CAC CAC TGG AGC GAT GTG TTG    1031
Leu Ser Arg Val Ser Asp Tyr Lys His His Trp Ser Asp Val Leu
                220                 225                    230
ACT GGA CTC ATT CAG GGA GCT CTG GTT GCA ATA TTA GTT GCT GTA    1076
Thr Gly Leu Ile Gln Gly Ala Leu Val Ala Ile Leu Val Ala Val
            235                 240                    245
TAT GTA TCG GAT TTC TTC AAA GAA AGA ACT TCT TTT AAA GAA AGA    1121
Tyr Val Ser Asp Phe Phe Lys Glu Arg Thr Ser Phe Lys Glu Arg
                250                 255                    260
AAA GAG GAG GAC TCT CAT ACA ACT CTG CAT GAA ACA CCA ACA ACT    1166
Lys Glu Glu Asp Ser His Thr Thr Leu His Glu Thr Pro Thr Thr
            265                 270                    275
GGG AAT CAC TAT CCG AGC AAT CAC CAG CCT TGA AAGGCAGCAGGGTGCC    1215
Gly Asn His Tyr Pro Ser Asn His Gln Pro ***
            280                 285
CAGGTGAAGCTGGCCTGTTTTCTAAAGGAAAATGATTGCCACAAGGCAAGAGGATGCATC   1275
TTTCTTCCTGGTGTACAAGCCTTTAAAGACTTCTGCTGCTGATATGCCTCTTGGATGCAC   1335
ACTTTGTGTGTACATAGTTACCTTTAACTCAGTGGTTATCTAATAGCTCTTTAAACTCATTA 1395
AAAAAACTCCAAGCCTTCCACCAAAACAGTGCCCCACCTGTATACATTTTTATTAAAAAA   1455
ATGTAATGCTTATGTATAAACATGTATGTAATATGCTTTCTATGAATGATGTTTGATTTA   1515
AATATAATACATATTAAAATGTATGGGAGAACCAAAAAAAAAAAAAAAAAA            1566
```

Fig. 3

```
GGCGCAGCTCTGCAAAAGTTTCTGCTCGGGATCTGGCTCTCTTCCCCTTGGACTTTAGAACG      62
ATTTAGGGTTGACAGAGGAAAGCAGAGGCGCGCAGGAGGAGCAGAAAACACCACCTTCTG       122
CAGTTGGAGGCAGGCAGCCCCGGCTGCACTCTAGCCGCCGCGCCCGGAGCCGGGGCCGAC       182
CCGCCACTATCCGCAGCAGCCTCGGCCAGGAGGCGACCCGGGCGCCTGGGTGTGTGGCTG       242
CTGTTGCGGGACGTCTTCGCGGGGCGGGAGGCTCGCGCCGCAGCCAGCGCC ATG CAA       299
                                                    Met Gln
```

| | | | | | | | | | | | | | | |
|---|---|---|---|---|---|---|---|---|---|---|---|---|---|---|
| AAC | TAC | AAG | TAC | GAC | AAA | GCG | ATC | GTC | CCG | GAG | AGC | AAG | AAC | GGC | 344
| Asn | Tyr | Lys | Tyr | Asp | Lys | Ala | Ile | Val | Pro | Glu | Ser | Lys | Asn | Gly |
| | | | 5 | | | | | 10 | | | | | 15 | |
| GGC | AGC | CCG | GCG | CTC | AAC | AAC | AAC | CCG | AGG | AGG | AGC | GGC | AGC | AAG | 389
| Gly | Ser | Pro | Ala | Leu | Asn | Asn | Asn | Pro | Arg | Arg | Ser | Gly | Ser | Lys |
| | | 20 | | | | | 25 | | | | | 30 | | |
| CGG | GTG | CTG | CTC | ATC | TGC | CTC | GAC | CTC | TTC | TGC | CTC | TTC | ATG | GCG | 434
| Arg | Val | Leu | Leu | Ile | Cys | Leu | Asp | Leu | Phe | Cys | Leu | Phe | Met | Ala |
| | | | 35 | | | | | 40 | | | | | 45 | |
| GGC | CTC | CCC | TTC | CTC | ATC | ATC | GAG | ACA | AGC | ACC | ATC | AAG | CCT | TAC | 479
| Gly | Leu | Pro | Phe | Leu | Ile | Ile | Glu | Thr | Ser | Thr | Ile | Lys | Pro | Tyr |
| | | 50 | | | | | 55 | | | | | 60 | | |
| CAC | CGA | GGG | TTT | TAC | TGC | AAT | GAT | GAG | AGC | ATC | AAG | TAC | CCA | CTG | 524
| His | Arg | Gly | Phe | Tyr | Cys | Asn | Asp | Glu | Ser | Ile | Lys | Tyr | Pro | Leu |
| | | | 65 | | | | | 70 | | | | | 75 | |
| AAA | ACT | GGT | GAG | ACA | ATA | AAT | GAC | GCT | GTG | CTC | TGT | GCC | GTG | GGG | 569
| Lys | Thr | Gly | Glu | Thr | Ile | Asn | Asp | Ala | Val | Leu | Cys | Ala | Val | Gly |
| | | 80 | | | | | 85 | | | | | 90 | | |
| ATC | GTC | ATT | GCC | ATC | CTC | GCG | ATC | ATC | ACG | GGG | GAA | TTC | TAC | CGG | 614
| Ile | Val | Ile | Ala | Ile | Leu | Ala | Ile | Ile | Thr | Gly | Glu | Phe | Tyr | Arg |
| | | | 95 | | | | | 100 | | | | | 105 | |
| ATC | TAT | TAC | CTG | AAG | AAG | TCG | CGG | TCG | ACG | ATT | CAG | AAC | CCC | TAC | 659
| Ile | Tyr | Tyr | Leu | Lys | Lys | Ser | Arg | Ser | Thr | Ile | Gln | Asn | Pro | Tyr |
| | | 110 | | | | | 115 | | | | | 120 | | |
| GTG | GCA | GCA | CTC | TAT | AAG | CAA | GTG | GGC | TGC | TTC | CTC | TTT | GGC | TGT | 704
| Val | Ala | Ala | Leu | Tyr | Lys | Gln | Val | Gly | Cys | Phe | Leu | Phe | Gly | Cys |
| | | | 125 | | | | | 130 | | | | | 135 | |
| GCC | ATC | AGC | CAG | TCT | TTC | ACA | GAC | ATT | GCC | AAA | GTG | TCC | ATA | GGG | 749
| Ala | Ile | Ser | Gln | Ser | Phe | Thr | Asp | Ile | Ala | Lys | Val | Ser | Ile | Gly |
| | | 140 | | | | | 135 | | | | | 150 | | |
| CGC | CTG | CGT | CCT | CAC | TTC | TTG | AGT | GTC | TGC | AAC | CCT | GAT | TTC | AGC | 794
| Arg | Leu | Arg | Pro | His | Phe | Leu | Ser | Val | Cys | Asn | Pro | Asp | Phe | Ser |
| | | | 155 | | | | | 160 | | | | | 165 | |
| CAG | ATC | AAC | TGC | TCT | GAA | GGC | TAC | ATT | CAG | AAC | TAC | AGA | TGC | AGA | 839
| Gln | Ile | Asn | Cys | Ser | Glu | Gly | Tyr | Ile | Gln | Asn | Tyr | Arg | Cys | Arg |
| | | 170 | | | | | | | | | | 180 | | |
| GGT | GAT | GAC | AGC | AAA | GTC | CAG | GAA | GCC | AGG | AAG | TCC | TTC | TTC | TCT | 884
| Gly | Asp | Asp | Ser | Lys | Val | Gln | Glu | Ala | Arg | Lys | Ser | Phe | Phe | Ser |
| | | | 185 | | | | | 190 | | | | | 195 | |
| GGC | CAT | GCC | TCC | TTC | TCC | ATG | TAC | ACT | ATG | CTG | TAT | TTG | GTG | CTA | 929
| Gly | His | Ala | Ser | Phe | Ser | Met | Tyr | Thr | Met | Leu | Tyr | Leu | Val | Leu |
| | | 200 | | | | | 205 | | | | | 210 | | |
| TAC | CTG | CAG | GCC | CGC | TTC | ACT | TGG | CGA | GGA | GCC | CGC | CTG | CTC | CGG | 974
| Tyr | Leu | Gln | Ala | Arg | Phe | Thr | Trp | Arg | Gly | Ala | Arg | Leu | Leu | Arg |
| | | | 215 | | | | | 220 | | | | | 225 | |
| CCC | CTC | CTG | CAG | TTC | ACC | TTG | ATC | ATG | ATG | GCC | TTC | TAC | ACG | GGA | 1019
| Pro | Leu | Leu | Gln | Phe | Thr | Leu | Ile | Met | Met | Ala | Phe | Tyr | Thr | Gly |
| | | 230 | | | | | 235 | | | | | 240 | | |
| CTG | TCT | CGC | GTA | TCA | GAC | CAC | AAG | CAC | CAT | CCC | AGT | GAT | GTT | CTG | 1064
| Leu | Ser | Arg | Val | Ser | Asp | His | Lys | His | His | Pro | Ser | Asp | Val | Leu |
| | | | 245 | | | | | 250 | | | | | 255 | |
| GCA | GGA | TTT | GCT | CAA | GGA | GCC | CTG | GTG | GCC | TGC | TGC | ATA | GTT | TTC | 1109
| Ala | Gly | Phe | Ala | Gln | Gly | Ala | Leu | Val | Ala | Cys | Cys | Ile | Val | Phe |
| | | 260 | | | | | 265 | | | | | 270 | | |
| TTC | GTG | TCT | GAC | CTC | TTC | AAG | ACT | AAG | ACG | ACG | CTC | TCC | CTG | CCT | 1154
| Phe | Val | Ser | Asp | Leu | Phe | Lys | Thr | Lys | Thr | Thr | Leu | Ser | Leu | Pro |
| | | | 275 | | | | | 280 | | | | | 285 | |
| GCC | CCT | GCT | ATC | CGG | AAG | GAA | ATC | CTT | TCA | CCT | GTG | GAC | ATT | ATT | 1199
| Ala | Pro | Ala | Ile | Arg | Lys | Glu | Ile | Leu | Ser | Pro | Val | Asp | Ile | Ile |
| | | 290 | | | | | 295 | | | | | 300 | | |
| GAC | AGG | AAC | AAT | CAC | CAC | AAC | ATG | ATG | TAG | GTGCCACCCACCTCCTGAGC | | | | | 1249
| Asp | Arg | Asn | Asn | His | His | Asn | Met | Met | *** | | | | | |
| | | | 305 | | | | | 310 | | | | | | |

```
TGTTTTTGTAAAATGACTGCTGACAGCAAGTTCTTGCTGCTCTCCAATCTCATCAGACAG     1309
TAGAATGTAGGGAAAAACTTTTGCCCGACTGATTTTTAAAAAAAAAAAAAAAAA           1362
```

Fig. 4

```
ACC ATG CAG CGG AGG TGG GTC TTC GTG CTG CTC GAC GTG CTG TGC    47
    Met Gln Arg Arg Trp Val Phe Val Leu Leu Asp Val Leu Cys
                     5                   10
TTA CTG GTC GCC TCC CTG CCC TTC GCT ATC CTG ACG CTG GTG AAC    92
Leu Leu Val Ala Ser Leu Pro Phe Ala Ile Leu Thr Leu Val Asn
 15                  20                  25
GCC CCG TAC AAG CGA GGA TTT TAC TGC GGG GAT GAC TCC ATC CGG   137
Ala Pro Tyr Lys Arg Gly Phe Tyr Cys Gly Asp Asp Ser Ile Arg
 30              35                  40
TAC CCC TAC CGT CCA GAT ACC ATC ACC CAC GGG CTC ATG GCT GGG   182
Tyr Pro Tyr Arg Pro Asp Thr Ile Thr His Gly Leu Met Ala Gly
 45                  50                  55
GTC ACC ATC ACG GCC ACC GTC ATC CTT GTC TCG GCC GGG GAA GCC   227
Val Thr Ile Thr Ala Thr Val Ile Leu Val Ser Ala Gly Glu Ala
 60              65                      70
TAC CTG GTG TAC ACA GAC CGG CTC TAT TCT CGC TCG GAC TTC AAC   272
Tyr Leu Val Tyr Thr Asp Arg Leu Tyr Ser Arg Ser Asp Phe Asn
 75                  80                  85
AAC TAC GTG GCT GCT GTA TAC AAG GTG CTG GGG ACC TTC CTG TTT   317
Asn Tyr Val Ala Ala Val Tyr Lys Val Leu Gly Thr Phe Leu Phe
 90                  95                 100
GGG GCT GCC GTG AGC CAG TCT CTG ACA GAC CTG GCC AAG TAC ATG   362
Gly Ala Ala Val Ser Gln Ser Leu Thr Asp Leu Ala Lys Tyr Met
105                 110                 115
ATT GGG CGT CTG AAG CCC AAC TTC CTA GCC GTC TGC GAC CCC GAC   407
Ile Gly Arg Leu Lys Pro Asn Phe Leu Ala Val Cys Asp Pro Asp
120                 125                 130
TGG AGC CGG GTC AAC TGC TCG GTC TAT GTG CAG CTG GAG AAG GTG   452
Trp Ser Arg Val Asn Cys Ser Val Tyr Val Gln Leu Glu Lys Val
135                 140                 145
TGC AGG GGA AAC CCT GCT GAT GTC ACC GAG GCC AGG TTG TCT TTC   497
Cys Arg Gly Asn Pro Ala Asp Val Thr Glu Ala Arg Leu Ser Phe
150                 155                 160
TAC TCG GGA CAC TCT TCC TTT GGG ATG TAC TGC ATG GTG TTC TTG   542
Tyr Ser Gly His Ser Ser Phe Gly Met Tyr Cys Met Val Phe Leu
165                 170                 175
GCG CTG TAT GTG CAG GCA CGA CTC TGT TGG AAG TGG GCA CGG CTG   587
Ala Leu Tyr Val Gln Ala Arg Leu Cys Trp Lys Trp Ala Arg Leu
180                 185                 190
CTG CGA CCC ACA GTC CAG TTC TTC CTG GTG GCC TTT GCC CTC TAC   632
Leu Arg Pro Thr Val Gln Phe Phe Leu Val Ala Phe Ala Leu Tyr
195                 200                 205
GTG GGC TAC ACC CGC GTG TCT GAT TAC AAA CAC CAC TGG AGC GAT   677
Val Gly Tyr Thr Arg Val Ser Asp Tyr Lys His His Trp Ser Asp
210                 215                 220
GTC CTT GTT GGC CTC CTG CAG GGG GCA CTG GTG GCT GCC CTC ACT   722
Val Leu Val Gly Leu Leu Gln Gly Ala Leu Val Ala Ala Leu Thr
225                 230                 235
GTC TGC TAC ATC TCA GAC TTC TTC AAA GCC CGA CCC CCA CAG CAC   767
Val Cys Tyr Ile Ser Asp Phe Phe Lys Ala Arg Pro Pro Gln His
240                 245                 250
TGT CTG AAG GAG GAG GAG CTG GAA CGG AAG CCC AGC CTG TCA CTG   812
Cys Leu Lys Glu Glu Glu Leu Glu Arg Lys Pro Ser Leu Ser Leu
255                 260                 265
ACG TTG ACC CTG GGG CGA GGC TGA CCACAACCACTTATGGGATACCCGCACT  864
Thr Leu Thr Leu Gly Arg Gly ***
270                 275
CTTCTTCCTGAGGCCGGACCCCGCCCAGGCAGGGAGCTGCTGTGAGTCCAGCTGATGCCC  924
ACCCAGGTGGTCCCTCCAGCCTGGTTAGGCACTGAGGGTTCTGGACGGGCTCCAGGAACC  984
CTGGGCTGATGGGAGCAGTGAGCGGTTCCGCTGCCCCCTGCCCTGCACTGGACCAGGAGT 1044
CTGGAGATGCCTGGGTAGCCCTCAGCATTTGGAGGGGAACCTGTTCCCGTCGGTCCCCAA 1104
ATATCCCCTTCTTTTTATGGGGTTAAGGAAGGGACCGAGAGATCAGATAGTTGCTGTTTT 1164
GTAAAATGTAATGTATATGTGGTTTTTAGTAAAATAGGGCACCTGTTTCACAAAAAAAAA 1224
AAAAAAAAAA                                                    1234
```

Fig. 5

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
      (A) LENGTH: 1563 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 342..1193

(ix) FEATURE:
      (A) NAME/KEY: mat_peptide
      (B) LOCATION: 342..1193

-continued (xi) SEQUENCE DESCRIPTION: SEQ ID NO:1:

```
CCTGTGGGAG AGAGCGCCGG GATCCGGACG GGGTAGCAAC CGGGGCAGGC CGTGCCGGCT        60

GAGGAGGTCC TGAGGCTACA GAGCTGCCGC GGCTGGCACA CGAGCGCCTC GGCACTAACC       120

GAGTGTTCGC GGGGGCTGTG AGGGGAGGGC CCCGGGCGCC ATTGCTGGCG GTGGGAGCGC       180

CGCCCGGTCT CAGCCCGCCC TCGGCTGCTC TCCTCCTCCG GCTGGGAGGG GCCGTATCTC       240

GGGGCCGTCG CCAGCCCCGG CCCGGGCTCG ATAATCAAGG GCCTCGGCCG TCGTCCCGCA       300

CCTCATTCCA TCGCCCTTGC CGGGCAGCCC GGGCAGAGAC C ATG TTT GAC AAG          353
                                              Met Phe Asp Lys
                                                1
```

```
ACG CGG CTG CCG TAC GTG GCC CTC GAT GTG CTC TGC GTG TTG CTG GCT        401
Thr Arg Leu Pro Tyr Val Ala Leu Asp Val Leu Cys Val Leu Leu Ala
  5              10              15              20

GGA TTG CCT TTT GCA ATT CTT ACT TCA AGG CAT ACC CCC TTC CAA CGA        449
Gly Leu Pro Phe Ala Ile Leu Thr Ser Arg His Thr Pro Phe Gln Arg
             25              30              35

GGA GTA TTC TGT AAT GAT GAG TCC ATC AAG TAC CCT TAC AAA GAA GAC        497
Gly Val Phe Cys Asn Asp Glu Ser Ile Lys Tyr Pro Tyr Lys Glu Asp
         40              45              50

ACC ATA CCT TAT GCG TTA TTA GGT GGA ATA ATC ATT CCA TTC AGT ATT        545
Thr Ile Pro Tyr Ala Leu Leu Gly Gly Ile Ile Ile Pro Phe Ser Ile
     55              60              65

ATC GTT ATT ATT CTT GGA GAA ACC CTG TCT GTT TAC TGT AAC CTT TTG        593
Ile Val Ile Ile Leu Gly Glu Thr Leu Ser Val Tyr Cys Asn Leu Leu
 70              75              80

CAC TCA AAT TCC TTT ATC AGG AAT AAC TAC ATA GCC ACT ATT TAC AAA        641
His Ser Asn Ser Phe Ile Arg Asn Asn Tyr Ile Ala Thr Ile Tyr Lys
 85              90              95             100

GCC ATT GGA ACC TTT TTA TTT GGT GCA GCT GCT AGT CAG TCC CTG ACT        689
Ala Ile Gly Thr Phe Leu Phe Gly Ala Ala Ala Ser Gln Ser Leu Thr
            105             110             115

GAC ATT GCC AAG TAT TCA ATA GGC AGA CTG CGG CCT CAC TTC TTG GAT        737
Asp Ile Ala Lys Tyr Ser Ile Gly Arg Leu Arg Pro His Phe Leu Asp
        120             125             130

GTT TGT GAT CCA GAT TGG TCA AAA ATC AAC TGC AGC GAT GGT TAC ATT        785
Val Cys Asp Pro Asp Trp Ser Lys Ile Asn Cys Ser Asp Gly Tyr Ile
    135             140             145

GAA TAC TAC ATA TGT CGA GGG AAT GCA GAA AGA GTT AAG GAA GGC AGG        833
Glu Tyr Tyr Ile Cys Arg Gly Asn Ala Glu Arg Val Lys Glu Gly Arg
150             155             160

TTG TCC TTC TAT TCA GGC CAC TCT TCG TTT TCC ATG TAC TGC ATG CTG        881
Leu Ser Phe Tyr Ser Gly His Ser Ser Phe Ser Met Tyr Cys Met Leu
165             170             175             180

TTT GTG GCA CTT TAT CTT CAA GCC AGG ATG AAG GGA GAC TGG GCA AGA        929
Phe Val Ala Leu Tyr Leu Gln Ala Arg Met Lys Gly Asp Trp Ala Arg
            185             190             195

CTC TTA CGC CCC ACA CTG CAA TTT GGT CTT GTT GCC GTA TCC ATT TAT        977
Leu Leu Arg Pro Thr Leu Gln Phe Gly Leu Val Ala Val Ser Ile Tyr
        200             205             210

GTG GGC CTT TCT CGA GTT TCT GAT TAT AAA CAC CAC TGG AGC GAT GTG       1025
Val Gly Leu Ser Arg Val Ser Asp Tyr Lys His His Trp Ser Asp Val
    215             220             225

TTG ACT GGA CTC ATT CAG GGA GCT CTG GTT GCA ATA TTA GTT GCT GTA       1073
Leu Thr Gly Leu Ile Gln Gly Ala Leu Val Ala Ile Leu Val Ala Val
230             235             240

TAT GTA TCG GAT TTC TTC AAA GAA AGA ACT TCT TTT AAA GAA AGA AAA       1121
Tyr Val Ser Asp Phe Phe Lys Glu Arg Thr Ser Phe Lys Glu Arg Lys
245             250             255             260
```

```
GAG GAG GAC TCT CAT ACA ACT CTG CAT GAA ACA CCA ACA ACT GGG AAT       1169
Glu Glu Asp Ser His Thr Thr Leu His Glu Thr Pro Thr Thr Gly Asn
                265                 270                 275

CAC TAT CCG AGC AAT CAC CAG CCT TGAAAGGCAG CAGGGTGCCC AGGTGAAGCT       1223
His Tyr Pro Ser Asn His Gln Pro
                280

GGCCTGTTTT CTAAAGGAAA ATGATTGCCA CAAGGCAAGA GGATGCATCT TTCTTCCTGG      1283

TGTACAAGCC TTTAAAGACT TCTGCTGCTG ATATGCCTCT TGGATGCACA CTTTGTGTGT      1343

ACATAGTTAC CTTTAACTCA GTGGTTATCT AATAGCTCTA AACTCATTAA AAAAACTCCA      1403

AGCCTTCCAC CAAAACAGTG CCCCACCTGT ATACATTTTT ATTAAAAAAA TGTAATGCTT      1463

ATGTATAAAC ATGTATGTAA TATGCTTTCT ATGAATGATG TTTGATTTAA ATATAATACA      1523

TATTAAAATG TATGGGAGAA CCAAAAAAAA AAAAAAAAA                             1563
```

(2) INFORMATION FOR SEQ ID NO:2:

(i) SEQUENCE CHARACTERISTICS:
        (A) LENGTH: 284 amino acids
        (B) TYPE: amino acid
        (D) TOPOLOGY: linear (ii) MOLECULE TYPE: protein (xi) SEQUENCE DESCRIPTION: SEQ ID NO:2:

```
Met Phe Asp Lys Thr Arg Leu Pro Tyr Val Ala Leu Asp Val Leu Cys
 1               5                  10                  15

Val Leu Leu Ala Gly Leu Pro Phe Ala Ile Leu Thr Ser Arg His Thr
                20                  25                  30

Pro Phe Gln Arg Gly Val Phe Cys Asn Asp Glu Ser Ile Lys Tyr Pro
            35                  40                  45

Tyr Lys Glu Asp Thr Ile Pro Tyr Ala Leu Leu Gly Gly Ile Ile Ile
        50                  55                  60

Pro Phe Ser Ile Ile Val Ile Ile Leu Gly Glu Thr Leu Ser Val Tyr
 65                  70                  75                  80

Cys Asn Leu Leu His Ser Asn Ser Phe Ile Arg Asn Asn Tyr Ile Ala
                85                  90                  95

Thr Ile Tyr Lys Ala Ile Gly Thr Phe Leu Phe Gly Ala Ala Ala Ser
                100                 105                 110

Gln Ser Leu Thr Asp Ile Ala Lys Tyr Ser Ile Gly Arg Leu Arg Pro
            115                 120                 125

His Phe Leu Asp Val Cys Asp Pro Asp Trp Ser Lys Ile Asn Cys Ser
        130                 135                 140

Asp Gly Tyr Ile Glu Tyr Tyr Ile Cys Arg Gly Asn Ala Glu Arg Val
145                 150                 155                 160

Lys Glu Gly Arg Leu Ser Phe Tyr Ser Gly His Ser Ser Phe Ser Met
                165                 170                 175

Tyr Cys Met Leu Phe Val Ala Leu Tyr Leu Gln Ala Arg Met Lys Gly
                180                 185                 190

Asp Trp Ala Arg Leu Leu Arg Pro Thr Leu Gln Phe Gly Leu Val Ala
            195                 200                 205

Val Ser Ile Tyr Val Gly Leu Ser Arg Val Ser Asp Tyr Lys His His
        210                 215                 220

Trp Ser Asp Val Leu Thr Gly Leu Ile Gln Gly Ala Leu Val Ala Ile
225                 230                 235                 240

Leu Val Ala Val Tyr Val Ser Asp Phe Phe Lys Glu Arg Thr Ser Phe
```

-continued

```
                   245                  250                      255
Lys Glu Arg Lys Glu Glu Asp Ser His Thr Thr Leu His Glu Thr Pro
            260                  265                  270

Thr Thr Gly Asn His Tyr Pro Ser Asn His Gln Pro
        275                 280
```

(2) INFORMATION FOR SEQ ID NO:3:

(i) SEQUENCE CHARACTERISTICS:
        (A) LENGTH: 1566 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 342..1196

(ix) FEATURE:
        (A) NAME/KEY: mat_peptide
        (B) LOCATION: 342..1196

(xi) SEQUENCE DESCRIPTION: SEQ ID NO:3:

```
CCTGTGGGAG AGAGCGCCGG GATCCGGACG GGGTAGCAAC CGGGGCAGGC CGTGCCGGCT      60

GAGGAGGTCC TGAGGCTACA GAGCTGCCGC GGCTGGCACA CGAGCGCCTC GGCACTAACC     120

GAGTGTTCGC GGGGGCTGTG AGGGGAGGGC CCCGGGCGCC ATTGCTGGCG GTGGGAGCGC     180

CGCCCGGTCT CAGCCCGCCC TCGGCTGCTC TCCTCCTCCG GCTGGGAGGG GCCGTATCTC     240

GGGGCCGTCG CCAGCCCCGG CCCGGGCTCG ATAATCAAGG GCCTCGGCCG TCGTCCCGCA     300

CCTCATTCCA TCGCCCTTGC CGGGCAGCCC GGGCAGAGAC C ATG TTT GAC AAG         353
                                              Met Phe Asp Lys
                                                1

ACG CGG CTG CCG TAC GTG GCC CTC GAT GTG CTC TGC GTG TTG CTG GCT       401
Thr Arg Leu Pro Tyr Val Ala Leu Asp Val Leu Cys Val Leu Leu Ala
  5                  10                  15                  20

TCC ATG CCT ATG GCT GTT CTA AAA TTG GGC CAA ATA TAT CCA TTT CAG       449
Ser Met Pro Met Ala Val Leu Lys Leu Gly Gln Ile Tyr Pro Phe Gln
                 25                  30                  35

AGA GGC TTT TTC TGT AAA GAC AAC AGC ATC AAC TAT CCG TAC CAT GAC       497
Arg Gly Phe Phe Cys Lys Asp Asn Ser Ile Asn Tyr Pro Tyr His Asp
             40                  45                  50

AGT ACC GCC GCA TCC ACT GTC CTC ATC CTA GTG GGG GTT GGC TTG CCC       545
Ser Thr Ala Ala Ser Thr Val Leu Ile Leu Val Gly Val Gly Leu Pro
         55                  60                  65

GTT TCC TCT ATT ATT CTT GGA GAA ACC CTG TCT GTT TAC TGT AAC CTT       593
Val Ser Ser Ile Ile Leu Gly Glu Thr Leu Ser Val Tyr Cys Asn Leu
     70                  75                  80

TTG CAC TCA AAT TCC TTT ATC AGT AAT AAC TAC ATA GCC ACT ATT TAC       641
Leu His Ser Asn Ser Phe Ile Ser Asn Asn Tyr Ile Ala Thr Ile Tyr
 85                  90                  95                 100

AAA GCC ATT GGA ACC TTT TTA TTT GGT GCA GCT GCT AGT CAG TCC CTG       689
Lys Ala Ile Gly Thr Phe Leu Phe Gly Ala Ala Ala Ser Gln Ser Leu
                105                 110                 115

ACT GAC ATT GCC AAG TAT TCA ATA GGC AGA CTG CGG CCT CAC TTC TTG       737
Thr Asp Ile Ala Lys Tyr Ser Ile Gly Arg Leu Arg Pro His Phe Leu
            120                 125                 130

GAT GTT TGT GAT CCA GAT TGG TCA AAA ATC AAC TGC AGC GAT GGT TAC       785
Asp Val Cys Asp Pro Asp Trp Ser Lys Ile Asn Cys Ser Asp Gly Tyr
        135                 140                 145

ATT GAA TAC TAC ATA TGT CGA GGG AAT GCA GAA AGA GTT AAG GAA GGC       833
Ile Glu Tyr Tyr Ile Cys Arg Gly Asn Ala Glu Arg Val Lys Glu Gly
```

```
                    150                  155                  160
AGG TTG TCC TTC TAT TCA GGC CAC TCT TCG TTT TCC ATG TAC TGC ATG       881
Arg Leu Ser Phe Tyr Ser Gly His Ser Ser Phe Ser Met Tyr Cys Met
165                 170                 175                 180

CTG TTT GTG GCA CTT TAT CTT CAA GCC AGG ATG AAG GGA GAC TGG GCA       929
Leu Phe Val Ala Leu Tyr Leu Gln Ala Arg Met Lys Gly Asp Trp Ala
                185                 190                 195

AGA CTC TTA CGC CCC ACA CTG CAA TTT GGT CTT GTT GCC GTA TCC ATT       977
Arg Leu Leu Arg Pro Thr Leu Gln Phe Gly Leu Val Ala Val Ser Ile
            200                 205                 210

TAT GTG GGC CTT TCT CGA GTT TCT GAT TAT AAA CAC CAC TGG AGC GAT      1025
Tyr Val Gly Leu Ser Arg Val Ser Asp Tyr Lys His His Trp Ser Asp
        215                 220                 225

GTG TTG ACT GGA CTC ATT CAG GGA GCT CTG GTT GCA ATA TTA GTT GCT      1073
Val Leu Thr Gly Leu Ile Gln Gly Ala Leu Val Ala Ile Leu Val Ala
    230                 235                 240

GTA TAT GTA TCG GAT TTC TTC AAA GAA AGA ACT TCT TTT AAA GAA AGA      1121
Val Tyr Val Ser Asp Phe Phe Lys Glu Arg Thr Ser Phe Lys Glu Arg
245                 250                 255                 260

AAA GAG GAG GAC TCT CAT ACA ACT CTG CAT GAA ACA CCA ACA ACT GGG      1169
Lys Glu Glu Asp Ser His Thr Thr Leu His Glu Thr Pro Thr Thr Gly
                265                 270                 275

AAT CAC TAT CCG AGC AAT CAC CAG CCT TGAAAGGCAG CAGGGTGCCC            1216
Asn His Tyr Pro Ser Asn His Gln Pro
            280                 285

AGGTGAAGCT GGCCTGTTTT CTAAAGGAAA ATGATTGCCA CAAGGCAAGA GGATGCATCT    1276

TTCTTCCTGG TGTACAAGCC TTTAAAGACT TCTGCTGCTG ATATGCCTCT TGGATGCACA    1336

CTTTGTGTGT ACATAGTTAC CTTTAACTCA GTGGTTATCT AATAGCTCTA AACTCATTAA    1396

AAAAACTCCA AGCCTTCCAC CAAAACAGTG CCCCACCTGT ATACATTTTT ATTAAAAAAA    1456

TGTAATGCTT ATGTATAAAC ATGTATGTAA TATGCTTTCT ATGAATGATG TTTGATTTAA    1516

ATATAATACA TATTAAAATG TATGGGAGAA CCAAAAAAAA AAAAAAAAA               1566

(2) INFORMATION FOR SEQ ID NO:4:

(i) SEQUENCE CHARACTERISTICS:
        (A) LENGTH: 285 amino acids
        (B) TYPE: amino acid
        (D) TOPOLOGY: linear (ii) MOLECULE TYPE: protein (xi) SEQUENCE DESCRIPTION: SEQ ID NO:4:

Met Phe Asp Lys Thr Arg Leu Pro Tyr Val Ala Leu Asp Val Leu Cys
1               5                   10                  15

Val Leu Leu Ala Ser Met Pro Met Ala Val Leu Lys Leu Gly Gln Ile
                20                  25                  30

Tyr Pro Phe Gln Arg Gly Phe Phe Cys Lys Asp Asn Ser Ile Asn Tyr
            35                  40                  45

Pro Tyr His Asp Ser Thr Ala Ala Ser Thr Val Leu Ile Leu Val Gly
        50                  55                  60

Val Gly Leu Pro Val Ser Ser Ile Ile Leu Gly Glu Thr Leu Ser Val
65                  70                  75                  80

Tyr Cys Asn Leu Leu His Ser Asn Ser Phe Ile Ser Asn Asn Tyr Ile
                85                  90                  95

Ala Thr Ile Tyr Lys Ala Ile Gly Thr Phe Leu Phe Gly Ala Ala Ala
            100                 105                 110
```

-continued

```
Ser Gln Ser Leu Thr Asp Ile Ala Lys Tyr Ser Ile Gly Arg Leu Arg
        115                 120                 125

Pro His Phe Leu Asp Val Cys Asp Pro Asp Trp Ser Lys Ile Asn Cys
    130                 135                 140

Ser Asp Gly Tyr Ile Glu Tyr Tyr Ile Cys Arg Gly Asn Ala Glu Arg
145                 150                 155                 160

Val Lys Glu Gly Arg Leu Ser Phe Tyr Ser Gly His Ser Ser Phe Ser
                165                 170                 175

Met Tyr Cys Met Leu Phe Val Ala Leu Tyr Leu Gln Ala Arg Met Lys
            180                 185                 190

Gly Asp Trp Ala Arg Leu Leu Arg Pro Thr Leu Gln Phe Gly Leu Val
        195                 200                 205

Ala Val Ser Ile Tyr Val Gly Leu Ser Arg Val Ser Asp Tyr Lys His
    210                 215                 220

His Trp Ser Asp Val Leu Thr Gly Leu Ile Gln Gly Ala Leu Val Ala
225                 230                 235                 240

Ile Leu Val Ala Val Tyr Val Ser Asp Phe Phe Lys Glu Arg Thr Ser
                245                 250                 255

Phe Lys Glu Arg Lys Glu Glu Asp Ser His Thr Thr Leu His Glu Thr
            260                 265                 270

Pro Thr Thr Gly Asn His Tyr Pro Ser Asn His Gln Pro
        275                 280                 285
```

(2) INFORMATION FOR SEQ ID NO:5:

(i) SEQUENCE CHARACTERISTICS:
      (A) LENGTH: 1362 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 294..1226

(ix) FEATURE:
      (A) NAME/KEY: mat_peptide
      (B) LOCATION: 294..1226

(xi) SEQUENCE DESCRIPTION: SEQ ID NO:5:

```
GGCGCAGCTC TGCAAAAGTT TCTGCTCGGG ATCTGGCTCT CTTCCCCTTG GACTTTAGAA      60

CGATTTAGGG TTGACAGAGG AAAGCAGAGG CGCGCAGGAG GAGCAGAAAA CACCACCTTC     120

TGCAGTTGGA GGCAGGCAGC CCCGGCTGCA CTCTAGCCGC CGCGCCCGGA GCCGGGGCCG     180

ACCCGCCACT ATCCGCAGCA GCCTCGGCCA GGAGGCGACC CGGGCGCCTG GGTGTGTGGC     240

TGCTGTTGCG GGACGTCTTC GCGGGGCGGG AGGCTCGCGC CGCAGCCAGC GCC ATG        296
                                                           Met
                                                             1

CAA AAC TAC AAG TAC GAC AAA GCG ATC GTC CCG GAG AGC AAG AAC GGC       344
Gln Asn Tyr Lys Tyr Asp Lys Ala Ile Val Pro Glu Ser Lys Asn Gly
        5                  10                  15

GGC AGC CCG GCG CTC AAC AAC AAC CCG AGG AGG AGC GGC AGC AAG CGG       392
Gly Ser Pro Ala Leu Asn Asn Asn Pro Arg Arg Ser Gly Ser Lys Arg
    20                  25                  30

GTG CTG CTC ATC TGC CTC GAC CTC TTC TGC CTC TTC ATG GCG GGC CTC       440
Val Leu Leu Ile Cys Leu Asp Leu Phe Cys Leu Phe Met Ala Gly Leu
35                  40                  45

CCC TTC CTC ATC ATC GAG ACA AGC ACC ATC AAG CCT TAC CAC CGA GGG       488
Pro Phe Leu Ile Ile Glu Thr Ser Thr Ile Lys Pro Tyr His Arg Gly
50                  55                  60                  65
```

```
TTT TAC TGC AAT GAT GAG AGC ATC AAG TAC CCA CTG AAA ACT GGT GAG    536
Phe Tyr Cys Asn Asp Glu Ser Ile Lys Tyr Pro Leu Lys Thr Gly Glu
             70                  75                  80

ACA ATA AAT GAC GCT GTG CTC TGT GCC GTG GGG ATC GTC ATT GCC ATC    584
Thr Ile Asn Asp Ala Val Leu Cys Ala Val Gly Ile Val Ile Ala Ile
             85                  90                  95

CTC GCG ATC ATC ACG GGG GAA TTC TAC CGG ATC TAT TAC CTG AAG AAG    632
Leu Ala Ile Ile Thr Gly Glu Phe Tyr Arg Ile Tyr Tyr Leu Lys Lys
             100                 105                 110

TCG CGG TCG ACG ATT CAG AAC CCC TAC GTG GCA GCA CTC TAT AAG CAA    680
Ser Arg Ser Thr Ile Gln Asn Pro Tyr Val Ala Ala Leu Tyr Lys Gln
         115                 120                 125

GTG GGC TGC TTC CTC TTT GGC TGT GCC ATC AGC CAG TCT TTC ACA GAC    728
Val Gly Cys Phe Leu Phe Gly Cys Ala Ile Ser Gln Ser Phe Thr Asp
130                 135                 140                 145

ATT GCC AAA GTG TCC ATA GGG CGC CTG CGT CCT CAC TTC TTG AGT GTC    776
Ile Ala Lys Val Ser Ile Gly Arg Leu Arg Pro His Phe Leu Ser Val
                 150                 155                 160

TGC AAC CCT GAT TTC AGC CAG ATC AAC TGC TCT GAA GGC TAC ATT CAG    824
Cys Asn Pro Asp Phe Ser Gln Ile Asn Cys Ser Glu Gly Tyr Ile Gln
                 165                 170                 175

AAC TAC AGA TGC AGA GGT GAT GAC AGC AAA GTC CAG GAA GCC AGG AAG    872
Asn Tyr Arg Cys Arg Gly Asp Asp Ser Lys Val Gln Glu Ala Arg Lys
             180                 185                 190

TCC TTC TTC TCT GGC CAT GCC TCC TTC TCC ATG TAC ACT ATG CTG TAT    920
Ser Phe Phe Ser Gly His Ala Ser Phe Ser Met Tyr Thr Met Leu Tyr
         195                 200                 205

TTG GTG CTA TAC CTG CAG GCC CGC TTC ACT TGG CGA GGA GCC CGC CTG    968
Leu Val Leu Tyr Leu Gln Ala Arg Phe Thr Trp Arg Gly Ala Arg Leu
210                 215                 220                 225

CTC CGG CCC CTC CTG CAG TTC ACC TTG ATC ATG ATG GCC TTC TAC ACG    1016
Leu Arg Pro Leu Leu Gln Phe Thr Leu Ile Met Met Ala Phe Tyr Thr
                 230                 235                 240

GGA CTG TCT CGC GTA TCA GAC CAC AAG CAC CAT CCC AGT GAT GTT CTG    1064
Gly Leu Ser Arg Val Ser Asp His Lys His His Pro Ser Asp Val Leu
                 245                 250                 255

GCA GGA TTT GCT CAA GGA GCC CTG GTG GCC TGC TGC ATA GTT TTC TTC    1112
Ala Gly Phe Ala Gln Gly Ala Leu Val Ala Cys Cys Ile Val Phe Phe
             260                 265                 270

GTG TCT GAC CTC TTC AAG ACT AAG ACG ACG CTC TCC CTG CCT GCC CCT    1160
Val Ser Asp Leu Phe Lys Thr Lys Thr Thr Leu Ser Leu Pro Ala Pro
275                 280                 285

GCT ATC CGG AAG GAA ATC CTT TCA CCT GTG GAC ATT ATT GAC AGG AAC    1208
Ala Ile Arg Lys Glu Ile Leu Ser Pro Val Asp Ile Ile Asp Arg Asn
290                 295                 300                 305

AAT CAC CAC AAC ATG ATG TAGGTGCCAC CCACCTCCTG AGCTGTTTTT           1256
Asn His His Asn Met Met
                 310

GTAAAATGAC TGCTGACAGC AAGTTCTTGC TGCTCTCCAA TCTCATCAGA CAGTAGAATG  1316

TAGGGAAAAA CTTTTGCCCG ACTGATTTTT AAAAAAAAAA AAAAAA              1362

(2) INFORMATION FOR SEQ ID NO:6:

(i) SEQUENCE CHARACTERISTICS:
        (A) LENGTH: 311 amino acids
        (B) TYPE: amino acid
        (D) TOPOLOGY: linear (ii) MOLECULE TYPE: protein
```

(xi) SEQUENCE DESCRIPTION: SEQ ID NO:6:

```
Met Gln Asn Tyr Lys Tyr Asp Lys Ala Ile Val Pro Glu Ser Lys Asn
  1               5                  10                  15

Gly Gly Ser Pro Ala Leu Asn Asn Pro Arg Arg Ser Gly Ser Lys
             20                  25                  30

Arg Val Leu Leu Ile Cys Leu Asp Leu Phe Cys Leu Phe Met Ala Gly
             35                  40                  45

Leu Pro Phe Leu Ile Ile Glu Thr Ser Thr Ile Lys Pro Tyr His Arg
         50                  55                  60

Gly Phe Tyr Cys Asn Asp Glu Ser Ile Lys Tyr Pro Leu Lys Thr Gly
 65              70                  75                  80

Glu Thr Ile Asn Asp Ala Val Leu Cys Ala Val Gly Ile Val Ile Ala
                 85                  90                  95

Ile Leu Ala Ile Ile Thr Gly Glu Phe Tyr Arg Ile Tyr Tyr Leu Lys
                100                 105                 110

Lys Ser Arg Ser Thr Ile Gln Asn Pro Tyr Val Ala Ala Leu Tyr Lys
                115                 120                 125

Gln Val Gly Cys Phe Leu Phe Gly Cys Ala Ile Ser Gln Ser Phe Thr
    130                 135                 140

Asp Ile Ala Lys Val Ser Ile Gly Arg Leu Arg Pro His Phe Leu Ser
145                 150                 155                 160

Val Cys Asn Pro Asp Phe Ser Gln Ile Asn Cys Ser Glu Gly Tyr Ile
                165                 170                 175

Gln Asn Tyr Arg Cys Arg Gly Asp Asp Ser Lys Val Gln Glu Ala Arg
                180                 185                 190

Lys Ser Phe Phe Ser Gly His Ala Ser Phe Ser Met Tyr Thr Met Leu
                195                 200                 205

Tyr Leu Val Leu Tyr Leu Gln Ala Arg Phe Thr Trp Arg Gly Ala Arg
    210                 215                 220

Leu Leu Arg Pro Leu Leu Gln Phe Thr Leu Ile Met Met Ala Phe Tyr
225                 230                 235                 240

Thr Gly Leu Ser Arg Val Ser Asp His Lys His His Pro Ser Asp Val
                245                 250                 255

Leu Ala Gly Phe Ala Gln Gly Ala Leu Val Ala Cys Cys Ile Val Phe
                260                 265                 270

Phe Val Ser Asp Leu Phe Lys Thr Lys Thr Thr Leu Ser Leu Pro Ala
    275                 280                 285

Pro Ala Ile Arg Lys Glu Ile Leu Ser Pro Val Asp Ile Ile Asp Arg
    290                 295                 300

Asn Asn His His Asn Met Met
305                 310
```

(2) INFORMATION FOR SEQ ID NO:7:

(i) SEQUENCE CHARACTERISTICS:
        (A) LENGTH: 1232 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 4..833

(ix) FEATURE:
        (A) NAME/KEY: mat_peptide
        (B) LOCATION: 4..833

(xi) SEQUENCE DESCRIPTION: SEQ ID NO:7:

```
ACC ATG CAG CGG AGG TGG GTC TTC GTG CTG CTC GAC GTG CTG TGC TTA        48
    Met Gln Arg Arg Trp Val Phe Val Leu Leu Asp Val Leu Cys Leu
    1               5                   10                  15

CTG GTC GCC TCC CTG CCC TTC GCT ATC CTG ACG CTG GTG AAC GCC CCG        96
Leu Val Ala Ser Leu Pro Phe Ala Ile Leu Thr Leu Val Asn Ala Pro
                20                  25                  30

TAC AAG CGA GGA TTT TAC TGC GGG GAT GAC TCC ATC CGG TAC CCC TAC       144
Tyr Lys Arg Gly Phe Tyr Cys Gly Asp Asp Ser Ile Arg Tyr Pro Tyr
                35                  40                  45

CGT CCA GAT ACC ATC ACC CAC GGG CTC ATG GCT GGG GTC ACC ATC ACG       192
Arg Pro Asp Thr Ile Thr His Gly Leu Met Ala Gly Val Thr Ile Thr
            50                  55                  60

GCC ACC GTC ATC CTT GTC TCG GCC GGG GAA GCC TAC CTG GTG TAC ACA       240
Ala Thr Val Ile Leu Val Ser Ala Gly Glu Ala Tyr Leu Val Tyr Thr
65                  70                  75

GAC CGG CTC TAT TCT CGC TCG GAC TTC AAC AAC TAC GTG GCT GCT GTA       288
Asp Arg Leu Tyr Ser Arg Ser Asp Phe Asn Asn Tyr Val Ala Ala Val
80                  85                  90                  95

TAC AAG GTG CTG GGG ACC TTC CTG TTT GGG GCT GCC GTG AGC CAG TCT       336
Tyr Lys Val Leu Gly Thr Phe Leu Phe Gly Ala Ala Val Ser Gln Ser
                100                 105                 110

CTG ACA GAC CTG GCC AAG TAC ATG ATT GGG CGT CTG AAG CCC AAC TTC       384
Leu Thr Asp Leu Ala Lys Tyr Met Ile Gly Arg Leu Lys Pro Asn Phe
            115                 120                 125

CTA GCC GTC TGC GAC CCC GAC TGG AGC CGG GTC AAC TGC TCG GTC TAT       432
Leu Ala Val Cys Asp Pro Asp Trp Ser Arg Val Asn Cys Ser Val Tyr
        130                 135                 140

GTG CAG CTG GAG AAG GTG TGC AGG GGA AAC CCT GCT GAT GTC ACC GAG       480
Val Gln Leu Glu Lys Val Cys Arg Gly Asn Pro Ala Asp Val Thr Glu
145                 150                 155

GCC AGG TTG TCT TTC TAC TCG GGA CAC TCT TCC TTT GGG ATG TAC TGC       528
Ala Arg Leu Ser Phe Tyr Ser Gly His Ser Ser Phe Gly Met Tyr Cys
160                 165                 170                 175

ATG GTG TTC TTG GCG CTG TAT GTG CAG GCA CGA CTC TGT TGG AAG TGG       576
Met Val Phe Leu Ala Leu Tyr Val Gln Ala Arg Leu Cys Trp Lys Trp
                180                 185                 190

GCA CGG CTG CTG CGA CCC ACA GTC CAG TTC TTC CTG GTG GCC TTT GCC       624
Ala Arg Leu Leu Arg Pro Thr Val Gln Phe Phe Leu Val Ala Phe Ala
            195                 200                 205

CTC TAC GTG GGC TAC ACC CGC GTG TCT GAT TAC AAA CAC CAC TGG AGC       672
Leu Tyr Val Gly Tyr Thr Arg Val Ser Asp Tyr Lys His His Trp Ser
        210                 215                 220

GAT GTC CTT GTT GGC CTC CTG CAG GGG GCA CTG GTG GCT GCC CTC ACT       720
Asp Val Leu Val Gly Leu Leu Gln Gly Ala Leu Val Ala Ala Leu Thr
    225                 230                 235

GTC TGC TAC ATC TCA GAC TTC TTC AAA GCC CGA CCC CCA CAG CAC TGT       768
Val Cys Tyr Ile Ser Asp Phe Phe Lys Ala Arg Pro Pro Gln His Cys
240                 245                 250                 255

CTG AAG GAG GAG GAG CTG GAA CGG AAG CCC AGC CTG TCA CTG ACG TTG       816
Leu Lys Glu Glu Glu Leu Glu Arg Lys Pro Ser Leu Ser Leu Thr Leu
                260                 265                 270

ACC CTG GGG CGA GGC TG ACCACAACCA CTTATGGGAT ACCCGCACTC                863
Thr Leu Gly Arg Gly
            275

TTCTTCCTGA GGCCGGACCC CGCCCAGGCA GGGAGCTGCT GTGAGTCCAG CTGATGCCCA      923

CCCAGGTGGT CCCTCCAGCC TGGTTAGGCA CTGAGGGTTC TGGACGGGCT CCAGGAACCC      983

TGGGCTGATG GGAGCAGTGA GCGGTTCCGC TGCCCCCTGC CCTGCACTGG ACCAGGAGTC     1043
```

-continued

```
TGGAGATGCC TGGGTAGCCC TCAGCATTTG GAGGGGAACC TGTTCCCGTC GGTCCCCAAA      1103

TATCCCCTTC TTTTTATGGG GTTAAGGAAG GGACCGAGAG ATCAGATAGT TGCTGTTTTG      1163

TAAAATGTAA TGTATATGTG GTTTTTAGTA AATAGGGCA CCTGTTTCAC AAAAAAAAAA       1223

AAAAAAAA                                                              1232
```

(2) INFORMATION FOR SEQ ID NO:8:

(i) SEQUENCE CHARACTERISTICS:
        (A) LENGTH: 276 amino acids
        (B) TYPE: amino acid
        (D) TOPOLOGY: linear (ii) MOLECULE TYPE: protein (xi) SEQUENCE DESCRIPTION: SEQ ID NO:8:

```
Met Gln Arg Arg Trp Val Phe Val Leu Leu Asp Val Leu Cys Leu Leu
 1               5                  10                  15

Val Ala Ser Leu Pro Phe Ala Ile Leu Thr Leu Val Asn Ala Pro Tyr
                20                  25                  30

Lys Arg Gly Phe Tyr Cys Gly Asp Asp Ser Ile Arg Tyr Pro Tyr Arg
            35                  40                  45

Pro Asp Thr Ile Thr His Gly Leu Met Ala Gly Val Thr Ile Thr Ala
        50                  55                  60

Thr Val Ile Leu Val Ser Ala Gly Glu Ala Tyr Leu Val Tyr Thr Asp
 65                  70                  75                  80

Arg Leu Tyr Ser Arg Ser Asp Phe Asn Asn Tyr Val Ala Ala Val Tyr
                85                  90                  95

Lys Val Leu Gly Thr Phe Leu Phe Gly Ala Ala Val Ser Gln Ser Leu
            100                 105                 110

Thr Asp Leu Ala Lys Tyr Met Ile Gly Arg Leu Lys Pro Asn Phe Leu
        115                 120                 125

Ala Val Cys Asp Pro Asp Trp Ser Arg Val Asn Cys Ser Val Tyr Val
    130                 135                 140

Gln Leu Glu Lys Val Cys Arg Gly Asn Pro Asp Val Thr Glu Ala
145                 150                 155                 160

Arg Leu Ser Phe Tyr Ser Gly His Ser Ser Phe Gly Met Tyr Cys Met
                165                 170                 175

Val Phe Leu Ala Leu Tyr Val Gln Ala Arg Leu Cys Trp Lys Trp Ala
            180                 185                 190

Arg Leu Leu Arg Pro Thr Val Gln Phe Phe Leu Val Ala Phe Ala Leu
        195                 200                 205

Tyr Val Gly Tyr Thr Arg Val Ser Asp Tyr Lys His His Trp Ser Asp
    210                 215                 220

Val Leu Val Gly Leu Leu Gln Gly Ala Leu Val Ala Ala Leu Thr Val
225                 230                 235                 240

Cys Tyr Ile Ser Asp Phe Phe Lys Ala Arg Pro Pro Gln His Cys Leu
                245                 250                 255

Lys Glu Glu Glu Leu Glu Arg Lys Pro Ser Leu Ser Leu Thr Leu Thr
            260                 265                 270

Leu Gly Arg Gly
        275
```

(2) INFORMATION FOR SEQ ID NO:9:

(i) SEQUENCE CHARACTERISTICS:

(A) LENGTH: 283 amino acids
      (B) TYPE: amino acid
      (C) STRANDEDNESS: single
      (D) TOPOLOGY: linear (xi) SEQUENCE DESCRIPTION: SEQ ID NO:9:

Met Phe Asp Lys Thr Arg Leu Pro Tyr Val Ala Leu Asp Val Ile Cys
1               5                  10                  15

Val Leu Leu Ala Gly Leu Pro Phe Ala Ile Leu Thr Ser Arg His Thr
            20                  25                  30

Pro Phe Gln Arg Gly Ile Phe Cys Asn Asp Asp Ser Ile Lys Tyr Pro
            35                  40                  45

Tyr Lys Glu Asp Thr Ile Pro Tyr Ala Leu Leu Gly Gly Ile Val Ile
        50                  55                  60

Pro Phe Cys Ile Ile Val Met Ser Ile Gly Glu Ser Leu Ser Val Tyr
65                  70                  75                  80

Phe Asn Val Leu His Ser Asn Ser Phe Val Gly Asn Pro Tyr Ile Ala
                85                  90                  95

Thr Ile Tyr Lys Ala Val Gly Ala Phe Leu Phe Gly Val Ser Ala Ser
            100                 105                 110

Gln Ser Leu Thr Asp Ile Ala Lys Tyr Thr Ile Gly Ser Leu Arg Pro
            115                 120                 125

His Phe Leu Ala Ile Cys Asn Pro Asp Trp Ser Lys Ile Asn Cys Ser
        130                 135                 140

Asp Gly Tyr Ile Glu Asp Tyr Ile Cys Gln Gly Asn Glu Glu Lys Val
145                 150                 155                 160

Lys Glu Gly Arg Leu Ser Phe Tyr Ser Gly His Ser Ser Phe Ser Met
                165                 170                 175

Tyr Cys Met Leu Phe Val Ala Leu Tyr Leu Gln Ala Arg Met Lys Gly
            180                 185                 190

Asp Trp Ala Arg Leu Leu Arg Pro Met Leu Gln Phe Gly Leu Ile Ala
        195                 200                 205

Phe Ser Ile Tyr Val Gly Leu Ser Arg Val Ser Asp Tyr Lys His His
        210                 215                 220

Trp Ser Asp Val Thr Val Gly Leu Ile Gln Gly Ala Ala Met Ala Ile
225                 230                 235                 240

Leu Val Ala Leu Tyr Val Ser Asp Phe Phe Lys Asp Thr His Ser Tyr
                245                 250                 255

Lys Glu Arg Lys Glu Glu Asp Pro His Thr Thr Leu His Glu Thr Ala
            260                 265                 270

Ser Ser Arg Asn Tyr Ser Thr Asn His Glu Pro
        275                 280

(2) INFORMATION FOR SEQ ID NO:10:

(i) SEQUENCE CHARACTERISTICS:
        (A) LENGTH: 284 amino acids
        (B) TYPE: amino acid
        (C) STRANDEDNESS: single
        (D) TOPOLOGY: linear (xi) SEQUENCE DESCRIPTION: SEQ ID NO:10:

Met Phe Asp Lys Thr Arg Leu Pro Tyr Val Ala Leu Asp Val Leu Cys
1               5                  10                  15

Val Leu Leu Ala Gly Leu Pro Phe Ala Ile Leu Thr Ser Arg His Thr
            20                  25                  30

Pro Phe Gln Arg Gly Val Phe Cys Asn Asp Glu Ser Ile Lys Tyr Pro

-continued

```
                35                  40                  45
Tyr Lys Glu Asp Thr Ile Pro Tyr Ala Leu Leu Gly Gly Ile Ile Ile
     50                  55                  60

Pro Phe Ser Ile Ile Val Ile Ile Leu Gly Glu Thr Leu Ser Val Tyr
 65                  70                  75                  80

Cys Asn Leu Leu His Ser Asn Ser Phe Ile Arg Asn Asn Tyr Ile Ala
                 85                  90                  95

Thr Ile Tyr Lys Ala Ile Gly Thr Phe Leu Phe Gly Ala Ala Ala Ser
            100                 105                 110

Gln Ser Leu Thr Asp Ile Ala Lys Tyr Ser Ile Gly Arg Leu Arg Pro
            115                 120                 125

His Phe Leu Asp Val Cys Asp Pro Asp Trp Ser Lys Ile Asn Cys Ser
        130                 135                 140

Asp Gly Tyr Ile Glu Tyr Tyr Ile Cys Arg Gly Asn Ala Glu Arg Val
145                 150                 155                 160

Lys Glu Gly Arg Leu Ser Phe Tyr Ser Gly His Ser Ser Phe Ser Met
                165                 170                 175

Tyr Cys Met Leu Phe Val Ala Leu Tyr Leu Gln Ala Arg Met Lys Gly
            180                 185                 190

Asp Trp Ala Arg Leu Leu Arg Pro Thr Leu Gln Phe Gly Leu Val Ala
        195                 200                 205

Val Ser Ile Tyr Val Gly Leu Ser Arg Val Ser Asp Tyr Lys His His
210                 215                 220

Trp Ser Asp Val Leu Thr Gly Leu Ile Gln Gly Ala Leu Val Ala Ile
225                 230                 235                 240

Leu Val Ala Val Tyr Val Ser Asp Phe Phe Lys Glu Arg Thr Ser Phe
                245                 250                 255

Lys Glu Arg Lys Glu Glu Asp Ser His Thr Thr Leu His Glu Thr Pro
            260                 265                 270

Thr Thr Gly Asn His Tyr Pro Ser Asn His Gln Pro
            275                 280
```

(2) INFORMATION FOR SEQ ID NO:11:

(i) SEQUENCE CHARACTERISTICS:
        (A) LENGTH: 285 amino acids
        (B) TYPE: amino acid
        (C) STRANDEDNESS: single
        (D) TOPOLOGY: linear (xi) SEQUENCE DESCRIPTION: SEQ ID NO:11:

```
Met Phe Asp Lys Thr Arg Leu Pro Tyr Val Ala Leu Asp Val Leu Cys
 1               5                  10                  15

Val Leu Leu Ala Ser Met Pro Met Ala Val Leu Lys Leu Gly Gln Ile
             20                  25                  30

Tyr Pro Phe Gln Arg Gly Phe Phe Cys Lys Asp Asn Ser Ile Asn Tyr
         35                  40                  45

Pro Tyr His Asp Ser Thr Ala Ala Ser Thr Val Leu Ile Leu Val Gly
     50                  55                  60

Val Gly Leu Pro Val Ser Ser Ile Ile Leu Gly Glu Thr Leu Ser Val
 65                  70                  75                  80

Tyr Cys Asn Leu Leu His Ser Asn Ser Phe Ile Arg Asn Asn Tyr Ile
                 85                  90                  95

Ala Thr Ile Tyr Lys Ala Ile Gly Thr Phe Leu Phe Gly Ala Ala Ala
            100                 105                 110
```

```
Ser Gln Ser Leu Thr Asp Ile Ala Lys Tyr Ser Ile Gly Arg Leu Arg
        115                 120                 125

Pro His Phe Leu Asp Val Cys Asp Pro Asp Trp Ser Lys Ile Asn Cys
        130                 135                 140

Ser Asp Gly Tyr Ile Glu Tyr Tyr Ile Cys Arg Gly Asn Ala Glu Arg
145                 150                 155                 160

Val Lys Glu Gly Arg Leu Ser Phe Tyr Ser Gly His Ser Ser Phe Ser
                165                 170                 175

Met Tyr Cys Met Leu Phe Val Ala Leu Tyr Leu Gln Ala Arg Met Lys
                180                 185                 190

Gly Asp Trp Ala Arg Leu Leu Arg Pro Thr Leu Gln Phe Gly Leu Val
                195                 200                 205

Ala Val Ser Ile Tyr Val Gly Leu Ser Arg Val Ser Asp Tyr Lys His
        210                 215                 220

His Trp Ser Asp Val Leu Thr Gly Leu Ile Gln Gly Ala Leu Val Ala
225                 230                 235                 240

Ile Leu Val Ala Val Tyr Val Ser Asp Phe Phe Lys Glu Arg Thr Ser
                245                 250                 255

Phe Lys Glu Arg Lys Glu Glu Asp Ser His Thr Thr Leu His Glu Thr
                260                 265                 270

Pro Thr Thr Gly Asn His Tyr Pro Ser Asn His Gln Pro
        275                 280                 285

(2) INFORMATION FOR SEQ ID NO:12:

(i) SEQUENCE CHARACTERISTICS:
        (A) LENGTH: 311 amino acids
        (B) TYPE: amino acid
        (C) STRANDEDNESS: single
        (D) TOPOLOGY: linear (xi) SEQUENCE DESCRIPTION: SEQ ID NO:12:

Met Gln Asn Tyr Lys Tyr Asp Lys Ala Ile Val Pro Glu Ser Lys Asn
1               5                   10                  15

Gly Gly Ser Pro Ala Leu Asn Asn Asn Pro Arg Arg Ser Gly Ser Lys
                20                  25                  30

Arg Val Leu Leu Ile Cys Leu Asp Leu Phe Cys Leu Phe Met Ala Gly
                35                  40                  45

Leu Pro Phe Leu Ile Ile Glu Thr Ser Thr Ile Lys Pro Tyr His Arg
        50                  55                  60

Gly Phe Tyr Cys Asn Asp Glu Ser Ile Lys Tyr Pro Leu Lys Thr Gly
65                  70                  75                  80

Glu Thr Ile Asn Asp Ala Val Leu Cys Ala Val Gly Ile Val Ile Ala
                85                  90                  95

Ile Leu Ala Ile Ile Thr Gly Glu Phe Tyr Arg Ile Tyr Tyr Leu Lys
                100                 105                 110

Lys Ser Arg Ser Thr Ile Gln Asn Pro Tyr Val Ala Ala Leu Tyr Lys
        115                 120                 125

Gln Val Gly Cys Phe Leu Phe Gly Cys Ala Ile Ser Gln Ser Phe Thr
        130                 135                 140

Asp Ile Ala Lys Val Ser Ile Gly Arg Leu Arg Pro His Phe Leu Ser
145                 150                 155                 160

Val Cys Asn Pro Asp Phe Ser Gln Ile Asn Cys Ser Glu Gly Tyr Ile
                165                 170                 175

Gln Asn Tyr Arg Cys Arg Gly Asp Asp Ser Lys Val Gln Glu Ala Arg
                180                 185                 190
```

```
Lys Ser Phe Phe Ser Gly His Ala Ser Phe Ser Met Tyr Thr Met Leu
        195                 200                 205

Tyr Leu Val Leu Tyr Leu Gln Ala Arg Phe Thr Trp Arg Gly Ala Arg
    210                 215                 220

Leu Leu Arg Pro Leu Leu Gln Phe Thr Leu Ile Met Met Ala Phe Tyr
225                 230                 235                 240

Thr Gly Leu Ser Arg Val Ser Asp His Lys His Pro Ser Asp Val
                245                 250                 255

Leu Ala Gly Phe Ala Gln Gly Ala Leu Val Ala Cys Cys Ile Val Phe
                260                 265                 270

Phe Val Ser Asp Leu Phe Lys Thr Lys Thr Thr Leu Ser Leu Pro Ala
        275                 280                 285

Pro Ala Ile Arg Lys Glu Ile Leu Ser Pro Val Asp Ile Ile Asp Arg
        290                 295                 300

Asn Asn His His Asn Met Met
305                 310
```

(2) INFORMATION FOR SEQ ID NO:13:

(i) SEQUENCE CHARACTERISTICS:
        (A) LENGTH: 276 amino acids
        (B) TYPE: amino acid
        (C) STRANDEDNESS: single
        (D) TOPOLOGY: linear (xi) SEQUENCE DESCRIPTION: SEQ ID NO:13:

```
Met Gln Arg Arg Trp Val Phe Val Leu Leu Asp Val Leu Cys Leu Leu
1               5                   10                  15

Val Ala Ser Leu Pro Phe Ala Ile Leu Thr Leu Val Asn Ala Pro Tyr
            20                  25                  30

Lys Arg Gly Phe Tyr Cys Gly Asp Asp Ser Ile Arg Tyr Pro Tyr Arg
        35                  40                  45

Pro Asp Thr Ile Thr His Gly Leu Met Ala Gly Val Thr Ile Thr Ala
50                  55                  60

Thr Val Ile Leu Val Ser Ala Gly Glu Ala Tyr Leu Val Tyr Thr Asp
65                  70                  75                  80

Arg Leu Tyr Ser Arg Ser Asp Phe Asn Asn Tyr Val Ala Ala Val Tyr
                85                  90                  95

Lys Val Leu Gly Thr Phe Leu Phe Gly Ala Ala Val Ser Gln Ser Leu
            100                 105                 110

Thr Asp Leu Ala Lys Tyr Met Ile Gly Arg Leu Lys Pro Asn Phe Leu
        115                 120                 125

Ala Val Cys Asp Pro Asp Trp Ser Arg Val Asn Cys Ser Val Tyr Val
130                 135                 140

Gln Leu Glu Lys Val Cys Arg Gly Asn Pro Ala Asp Val Thr Glu Ala
145                 150                 155                 160

Arg Leu Ser Phe Tyr Ser Gly His Ser Ser Phe Gly Met Tyr Cys Met
                165                 170                 175

Val Phe Leu Ala Leu Tyr Val Gln Ala Arg Leu Cys Trp Lys Trp Ala
            180                 185                 190

Arg Leu Leu Arg Pro Thr Val Gln Phe Phe Leu Val Ala Phe Ala Leu
        195                 200                 205

Tyr Val Gly Tyr Thr Arg Val Ser Asp Tyr Lys His His Trp Ser Asp
        210                 215                 220

Val Leu Val Gly Leu Leu Gln Gly Ala Leu Val Ala Ala Leu Thr Val
```

```
                225                 230                 235                 240
Cys Tyr Ile Ser Asp Phe Phe Lys Ala Arg Pro Pro Gln His Cys Leu
                245                 250                 255

Lys Glu Glu Leu Glu Arg Lys Pro Ser Leu Ser Leu Thr Leu Thr
        260                 265                 270

Leu Gly Arg Gly
        275

(2) INFORMATION FOR SEQ ID NO:14:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:14:

GGCTCTAGAT ATTAATAGTA ATCAATTAC                                    29

(2) INFORMATION FOR SEQ ID NO:15:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:15:

CCTCACGCAT GCACCATGGT AATAGC                                       26

(2) INFORMATION FOR SEQ ID NO:16:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:16:

GGTGCATGCG TGAGGCTCCG GTGC                                         24

(2) INFORMATION FOR SEQ ID NO:17:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:17:

GTAGTTTTCA CGGTACCTGA AATGGAAG                                     28

(2) INFORMATION FOR SEQ ID NO:18:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:18:

GGCATGGTAC CATGTTTGAC AAGACGCGGC                                   30

(2) INFORMATION FOR SEQ ID NO:19:
```

-continued

```
    (i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:19:

CATATGTAGT ATTCAATGTA ACC                                              23

(2) INFORMATION FOR SEQ ID NO:20:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO:20:

TGATGGCTAG CATGCAGAGA AGATGGGTCT TCGTGCTGCT CGACGTG                    47

(2) INFORMATION FOR SEQ ID NO:21:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:21:

AGTGCGGGAT CCCATAAGTG GTTG                                             24
```

HUMAN PHOSPHATIDIC ACID PHOSPHATASE

FIELD OF THE INVENTION

This invention relates to human phosphatidic acid phosphatase. More particularly, this invention relates to three variants of human phosphatidic acid phosphatase namely PAP-α(1 and 2), PAP-β and PAP-γ and uses thereof. The invention encompasses biotechnology inventions, including biotechnology products and processes.

BACKGROUND OF THE INVENTION

Phosphatidic acid phosphatase (PAP) (also referred to in the art as phosphatidate phosphohydrolase) is known to be an important enzyme for glycerolipid biosynthesis. In particular, PAP catalyzes the conversion of phosphatidic acid (PA) (also referred to in the art as phosphatidate) into diacylglycerol (DAG). DAG is an important branch point intermediate just downstream of PA in the pathways for biosynthesis of glycerophosphate-based phospholipids (Kent, Anal. Rev. Biochem. 64: 315–343, 1995).

In eukaryotic cells, PA, the precursor molecule for all glycerophospholipids, is converted either to CDP-diacylglycerol (CDP-DAG) by CDP-DAG synthase (CDS) or to DAG by phosphatidic acid phosphatase (PAP). In mammalian cells, CDP-DAG is the precursor to phosphatidylinositol (PI), phosphatidylglycerol (PG), and cardiolipin (CL); whereas diacylglycerol is the precursor to triacylglycerol (TG), phosphatidylethanolamine (PE), and phosphatidylcholine (PC) in all eukaryotic cells. Therefore, the partitioning of phosphatidic acid between CDP-diacylglycerol and diacylglycerol is an important regulatory point in eukaryotic phospholipid metabolism (Shen et al., J. Biol. Chem. 271: 789–795, 1996).

In addition to being an important enzyme for glycerolipid biosynthesis, PAP is also an important enzyme for signal transduction. PAP catalyses the dephosphorylation of PA to DAG. DAG is a well-studied lipid second messenger which is essential for the activation of protein kinase C (Kent, Anal. Rev.Biochem. 64: 315–343, 1995); whereas PA itself is also a lipid messenger implicated in various signaling pathways such as NADPH oxidase activation and calcium mobilization (English, *Cell Signal.* 8: 341–347, 1996). The regulation of PAP activity can therefore affect the balance of divergent signaling processes that the cell receives in terms of PA and DAG (Brindley et al., Chem. Phys. Lipids 80: 45–57, 1996).

Various forms of PAP have been isolated in porcine (Kai et al., J. Biol. Chem. 271: 18931–18938, 1996) and rat species (Brindley et al., Chem. Phys. Lipids 80: 45–57, 1996). Furthermore, the putative amino acid sequence of murine PAP has been identified. Kai et al., supra. Prior to the instant invention, however, human PAP had not been identified or isolated.

Genes coding for PAP have been identified in *E. coli* (Dillon et al, J. Biol. Chem. 260: 12078–12083, 1985) and in mouse (Kai et al., J. Biol. Chem. 271: 18931–18938, 1996). Furthermore, the following GenBank human cDNA clones are available: accession nos. H17855, N75714, and W70040. No uses were known, however, for these polynucleotide sequences.

Accordingly, there is a need for the identification and isolation of human PAP and for methods of using human PAP, for example, for the dephosphorylation of a substrate.

SUMMARY OF THE INVENTION

It is therefore an object of the present invention to provide a polynucleotide sequences encoding three or more variants of human PAP, namely PAP-α(1 and 2), PAP-β and PAP-γ.

It is a further object to provide the isolated protein of these three variants.

It is yet a further object to provide a biotechnology method for preparing these variants via recombinant methods.

It is a further object to provide a biotechnology method of using these variants or human PA in general to synthesize DAG.

In accomplishing these and other objects there is provided an isolated polynucleotide encoding human phosphatidic acid phosphatase wherein the polynucleotide encodes a protein comprising a polypeptide sequence selected from the group consisting of (i) the sequence at amino acid number 1 to amino acid number 284 (SEQ ID NO: 2) FIG. 1, (ii) the sequence at amino acid number 1 to amino acid number 285 (SEQ ID NO: 4) in FIG. 2, and (iii) the sequence at amino acid number 1 to amino acid number 276 (SEQ ID NO:8) in FIG. 4.

There is further provided an isolated human phosphatidic acid phosphatase protein, wherein the protein comprises a polypeptide sequence selected from the group consisting of (i) the sequence at amino acid number 1 to amino acid 284 (SEQ ID NO:2) in FIG. 1, (ii) the sequence at amino acid number 1 to amino acid number 285 (SEQ ID NO:4) in FIG. 2, and (iii) the sequence at amino acid number 1 to amino acid number 276 (SEQ ID NO:8) in FIG. 4.

There if further provided a method of preparing a human phosphatidic acid phosphatase-β protein comprising the steps of (i) transforming a host cell with an expression vector comprising a polynucleotide encoding human phosphatidic acid phosphatase, (ii) culturing the transformed host cells which express the protein and (iii) isolating the protein.

There if further provided a method of dephosphorylating a substrate comprising contacting the substrate with an effective amount of isolated human phosphatidic acid phosphatase protein such that the protein catalyzes the dephosphorylation of the substrate. It is further provided that the substrate of this method is selected from the group consisting of phosphatidic acid, lysophosphatidic acid, ceramide 1-phosphate, and sphingosine 1-phosphate. It is further provided that this method occurs in vitro, and comprises a step of isolating the dephosphoryled substrate. Additionally, the method can occur in vivo, and is effected by the administration of human phosphatidic acid phosphatase to a mammal in need thereof.

BRIEF DESCRIPTION OF THE DRAWINGS

FIG. 1 shows the DNA sequence of the cDNA insert of the human PAP-α1 isolated herein and the corresponding amino acid sequence (SEQ ID NOS: 1 and 2).

FIG. 2 shows the DNA sequence of the cDNA insert of the human PAP-α2 isolated herein and the corresponding amino acid sequence (SEQ ID NOS: 3 and 4).

FIG. 3 shows the DNA sequence of the cDNA insert of the human PAP-β isolated herein and the corresponding amino acid sequence (SEQ ID NOS: 5 and 6).

FIG. 4 shows the DNA sequence of the cDNA insert of the human PAP-γ isolated herein and the corresponding amino acid sequence (SEQ ID NOS: 7 and 8).

Figure 5:
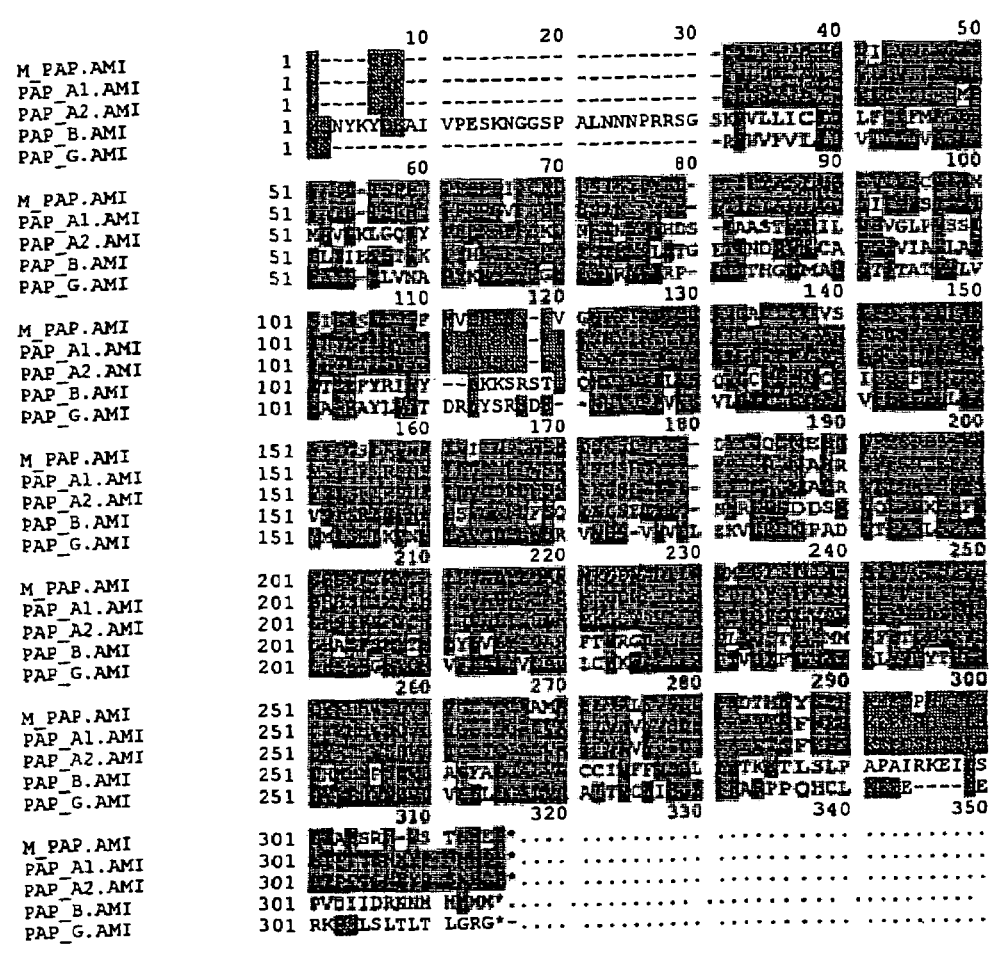

FIG. 5 shows amino acid sequences (SEQ ID NOS: 9–13) alignment of the murine PAP coding sequence and the coding sequences for human PAP-α(1 and 2), PAP-β and PAP-γ.

DETAILED DESCRIPTION OF PREFERRED EMBODIMENTS

Figure 6:
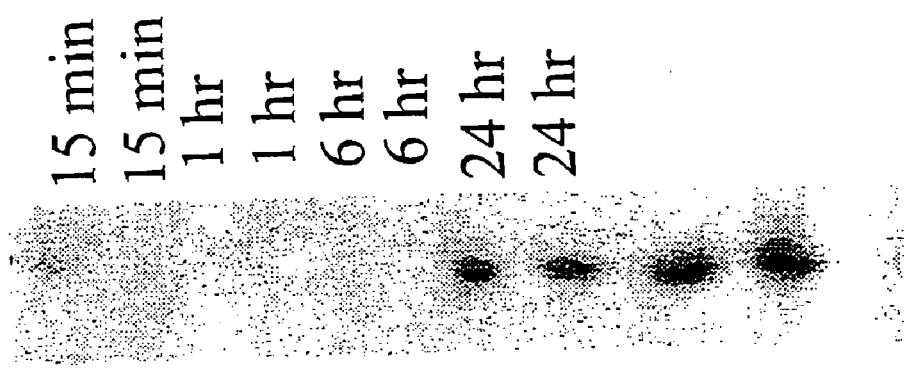
FIG. 6 shows the effect of IL-1β on PAP-β expression in human endothelial ECV304 cells using Northern blot analysis.

This invention relates to isolated human phosphatidic acid phosphatase. More particularly, this invention relates to three variants of human phosphatidic acid phosphatase namely PAP-α(1 and 2), PAP-β and PAP-γ.

Examples of the uses for human PAP include the following. PAP is an important tool for enzymatic catalysis of several biologically significant proteins. As discussed above, PAP catalyzes the dephosphorylation of PA to DAG. DAG, in turn, is essential for the activation of protein kinase C (Kent, Anal. Rev.Biochem. 64: 315–343, 1995).

Moreover, PAP catalyzes the dephosphorylation of lyso-phosphatidic acid (LPA), ceramide 1-phosphate (C-1-P), and sphingosine 1-phosphate (S-1-P) (Brindley et al., *Chem. Phys. Lipids* 80: 45–57, 1996). In the case of LPA, S-1-P, and C-1-P, the products of the PAP reaction are monoacylglycerol, sphingosine, and ceramide, respectively. PAP can control the balance of a wide spectrum of lipid mediators of cell activation and signal transduction by modulating the phosphorylated state of these lipids.

Additionally, the human PAP of the present invention are likely to define a new family of tumor suppressor genes that can be used as candidate genes for gene therapy for the treatment of certain tumors. The relationship of PAP and tumor suppression is evidenced in findings that PAP activity is lower in fibroblast cell lines transformed with either the ras or fps oncogene than in the parental rat1 cell line (Brindley et al., *Chem. Phys. Lipids* 80: 45–57, 1996). Decrease in PAP activity in transformed cells correlates with a concomitant increase in PA concentration. Moreover, elevated PAP activity and lower level of PA has been observed in contact-inhibited fibroblasts relative to proliferating and transformed fibroblasts (Brindley et al., *Chem. Phys. Lipids* 80: 45–57, 1996). Therefore, PAP plays a role in decreasing cell division and as such can provide a useful tool in treating cancer.

Additionally, PA, the substrate for the enzyme PAP, has been implicated in cytokine induced inflammatory responses (Bursten et al., Circ. Shock 44: 14–29, 1994; Abraham et al., J. Exp. Med. 181: 569–575, 1995; Rice et al., Proc. Natl. Acad. Sci. USA 91: 3857–3861 1994; Leung et al., Proc. Natl. Acad. Sci. USA 92: 4813–4817, 1995) and the modulation of numerous protein kinases involved in signal transduction (English et al., Chem. Phys. Lipids 80: 117–132, 1996). Because of the possibility that activation of human PAP expression can counter-balance the inflammatory response from cytokine stimulation through degradation of excess amount of PA in cells, the genes encoding human PAP can be used in gene therapy for the treatment of inflammatory diseases.

Human PAP described herein can also be used in gene therapy for the treatment of obesity associated with diabetes. PAP activity is decreased in the livers and hearts of the grossly obese and insulin resistant JCR:LA corpulent rat compared to the control lean phenotype (Brindley et al., *Chem. Phys. Lipids* 80: 45–57, 1996). Human PAP described herein therefore can provide an important tool for the treatment of obesity associated with diabetes.

1. Human PAP

As used herein, "phosphatidic acid phosphatase" or "PAP" refers to a protein capable of catalyzing the dephosphorylation of PA to DAG. PAP also includes proteins capable of catalyzing the dephosphorylation of lysophosphatidic acid (LPA), ceramide 1-phosphate (C-1-P), and sphingosine 1-phosphate (S-1-P).

As used herein, "isolated" PAP denotes a degree of separation of the protein from other materials endogenous to the host organism. As used herein, "purified" denotes a higher degree of separation than isolated. A purified protein is sufficiently free of other materials endogenous to the host organism such that any remaining materials do not adversely affect the biological properties of the protein, for example, a purified protein is one sufficiently pure to be used in a pharmaceutical context.

As used herein, "human" PAP refers to PAP naturally occurring (or "native") in the human species, including natural variations due to allelic differences. The term "human PAP," however, is not limited to native human proteins, but also includes amino acid sequence variants of native human PAP that demonstrate PAP activity, as defined above.

Variants often exhibit the same qualitative biological activity as the naturally-occurring analogue, although variants also are selected in order to modify the characteristics of PAP protein. In a preferred embodiment, therefore, human PAP includes the amino acid sequences of FIGS. 1–4 (SEQ ID NOS: 2, 4, 6 and 8), being PAP-α1, PAP-α2, PAP-β and PAP-γ, respectively an variants thereof.

Amino acid sequence variants of the protein can be substitutional, insertional or deletion variants. Deletion variants lack one or more residues of the native protein which are not essential for biological activity. An example of a common deletion variant is a protein lacking transmembrane sequences. Another example is a protein lacking secretory signal sequences or signal sequences directing the protein to bind to a particular part of a cell.

Substitutional variants typically contain the exchange of one amino acid for another at one or more sites within the protein, and are designed to modulate one or more properties of the protein such as stability against proteolytic cleavage. Substitutions preferably are conservative, that is, one amino acid is replaced with one of similar shape and charge. Conservative substitutions are well known in the art and include, for example, the changes of: alanine to serine; arginine to lysine; asparigine to glutamine or histidine; aspartate to glutamate; cysteine to serine; glutamine to asparigine; glutamate to aspartate; glycine to proline; histidine to asparigine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Of course, other amino acid substitutions can be undertaken.

Insertional variants contain fusion proteins such as those used to allow rapid purification of the protein and also can include hybrid proteins containing sequences from other proteins and polypeptides which are protein homologues.

Variants of human PAP also include fragments, analogs, derivatives, muteins and mimetics of the natural PAP protein that retain the ability to cause the beneficial results described above. Fragments of the human PAP protein refer to portions of the amino acid sequence of the PAP polypeptide that also retain this ability.

Variants can be generated directly from the human PAP protein itself by chemical modification by proteolytic enzyme digestion, or by combinations thereof. Additionally, methods of synthesizing polypeptides directly from amino acid residues also exist.

Non-peptide compounds that mimic the binding and function of the human PAP protein ("mimetics") can be produced by the approach outlined in Saragovi et al., *Science* 253: 792–95 (1991). Mimetics are peptide-containing molecules which mimic elements of protein secondary structure. See, for example, Johnson et al., "Peptide Turn Mimetics" in BIOTECHNOLOGY AND PHARMACY, Pezzuto et al., Eds., (Chapman and Hall, New York, 1993).

The underlying rationale behind the use of peptide mimetics is that the peptide backbone of proteins exists chiefly to orient amino acid side chains in such a way as to facilitate molecular interactions For the purposes of the present invention, appropriate mimetics can be considered to be the equivalent of the human PAP protein itself.

More typically, at least in the case of gene therapy, variants are created by recombinant techniques employing genomic or cDNA cloning methods. Site-specific and region-directed mutagenesis techniques can be employed. See CURRENT PROTOCOLS IN MOLECULAR BIOLOGY vol. 1, ch. 8 (Ausubel et al. eds., J. Wiley & Sons 1989 & Supp. 1990–93); PROTEIN ENGINEERING (Oxender & Fox eds., A. Liss, Inc. 1987). In addition, linker-scanning and PCR-mediated techniques can be employed for mutagenesis. See PCR TECHNOLOGY (Erlich ed., Stockton Press 1989); CURRENT PROTOCOLS IN MOLECULAR BIOLOGY, vols. 1 & 2, supra. Protein sequencing, structure and modeling approaches for use with any of the above techniques are disclosed in PROTEIN ENGINEERING, loc. cit. and CURRENT PROTOCOLS IN MOLECULAR BIOLOGY, vols. 1 & 2, supra.

2. Polynucleotides Encoding Human PAP

The present invention further includes isolated polynucleotides encoding human phosphatidic acid phosphatase. As used herein, an "isolated" polynucleotide denotes a degree of separation of the polynucleotide from its naturally occurring environment, e.g., from its native intact genome. In a preferred embodiment, the isolated polynucleotides correspond to those shown in FIG. 1 at nucleotide number 342 to nucleotide number 119 of SEQ ID NO: 1; FIG. 2 at nucleotide number 342 to nucleotide number 1196 of SEQ ID NO: 3; FIG. 3 at nucleotide number 294 to nucleotide number 1226 of SEQ ID NO:5 and FIG. 4 at nucleotide number 4 to nucleotide number 833 of SEQ ID NO:7.

The invention furthermore relates to a polynucleotide whose sequence is degenerate with respect to the sequences mentioned above in accordance with the nature of the genetic code. Degeneracy is often referred to as codon/anticodon wobble, and is discussed in Watson et al., *MOLECULAR BIOLOGY OF THE GENE* (4th ed. 1987) at 437–43.

The present invention further includes bases, nucleosides, nucleotides, oligonucleotides derived from the isolated polynucleotides of the present invention. The term "derived" when used in the context of the present invention connotes a degree of similarity that is sufficient to indicate the original polynucleotide from which hybrid forms, or portions thereof, were obtained. Also within the scope of the invention are so-called "polyamide" or "peptide" nucleic acids ("PNAs") derived from the polynucleotides of the present invention. PNAs are constructed by replacing the (deoxy) ribose phosphate backbone of a subject polynucleotide with an achiral polyamide backbone or the like. See Nielsen et al., *Science* 254: 1497–54 (1991).

The above polynucleotides and derivations thereof can be used as important tools in recombinant DNA and other protocols involving nucleic acid hybridization techniques. More specifically, oligonucleotides and nucleic acids derived from the isolated polynucleotides shown in FIGS. 1–4 (SEQ ID NOS: 1, 3, 5 and 7) can be used as hybridization probes, capable of recognizing and specifically binding to complementary nucleic acid sequences, providing thereby a means of detecting, identifying, locating and measuring complementary nucleic acid sequences in a biological sample.

Biological samples include, among a great many others, blood or blood serum, lymph, ascites fluid, urine, microorganism or tissue culture medium, cell extracts, or the like, derived from a biological source, or a solution containing chemically synthesized protein, or an extract or solution prepared from such fluid from a biological source.

An oligonucleotide containing a modified nucleotide of the invention can be used as a primer to initiate nucleic acid synthesis at locations in a DNA or RNA molecule comprising the sequence complementary to the oligonucleotide sequence. The synthesized nucleic acid strand would have incorporated, at its 5' terminus, the oligonucleotide primer bearing the invention and would, therefore, be detectable by exploitation of the characteristics of the detectable label. Two such primers, specific for different nucleotide sequences on complementary strands of dsDNA, can be used in the polymerase chain reaction (PCR) to synthesize and amplify the amount of a nucleotide sequence. The detectable label present on the primers will facilitate the identification of desired PCR products. PCR, combined with techniques for preparing complementary DNA (cDNA) can be used to amplify various RNAS, with oligonucleotide primers again serving both to provide points for initiation of synthesis in the cDNA duplex flanking the desired sequence and to identify the desired product. Primers labeled with the invention may also be utilized for enzymatic nucleic acid sequencing by the dideoxy chain-termination technique.

The invention can be applied to measure or quantitate the amount of DNA present in a sample. For instance, the concentration of nucleic acid can be measured by comparing detectable labels incorporated into the unknown nucleic acid with the concentration of detectable labels incorporated into known amounts of nucleic acid.

Such a comparative assessment can be done using biotin where the respective concentrations are determined by an enzyme-linked assay utilizing the streptavidin-alkaline phosphatase conjugate and a substrate yielding a soluble chromogenic or chemiluminescent signal.

3. Recombinant Production of Human PAP

In a further embodiment human PAP is expressed via recombinant methods known to those of skill in the art. The polynucleotides of the present invention can be expressed in any number of different recombinant DNA expression systems to generate large amounts of protein, which can then be purified and used for the various applications of human PAP described above. Included within the present invention are proteins having native glycosylation sequences, and deglycosylated or unglycosylated proteins prepared by the methods described below.

Recombinant technology for producing desired proteins is known by ordinarily skilled artisans and includes providing a coding sequence for a desired protein, and operably linking the coding sequence to polynucleotide sequences capable of effecting its expression.

With regard to one aspect of the invention, it often is desirable to produce human PAP as a fusion protein, freed from upstream, downstream or intermediate sequences, or as a protein linked to leader sequences, effecting secretion of human PAP into cell culture medium.

A typical expression system will also contain control sequences necessary for transcription and translation of a message. Known control sequences include constitutive or inducible promoter systems, translational initiation signals (in eucaryotic expression), polyadenylation translation termination sites, and transcription terminating sequences. Expression vectors containing controls which permit operably linking of desired coding sequences to required control systems are known by the skilled artisan. Such vectors can be found which are operable in a variety of hosts.

Human PAP of the present invention may be produced in procaryotic cells using appropriate controls, such as trp or lac promoters, or in eucaryotic host cells, capable of effecting post-translational processing that permits proteins to assume desired three-dimensional conformation. Eucaryotic control systems and expression vectors are known; including leu and glycolytic promoters useful in yeast, the viral SV40 and adenovirus and CMV promoters in mammalian cells, and the baculovirus system which is operable in insect cells. Plant vectors with suitable promoters, such as the nos promoter are also available.

Standard laboratory manuals (e.g., Sambrook et al., *MOLECULAR CLONING: A LABORATORY MANUAL*, Second Edition, (Cold Spring Harbor Laboratory Press, Cold Spring Harbor, N.Y. 1989) present standard techniques and methodologies for expressing polynucleotides encoding a desired protein, culturing appropriate cells, providing suitable expression conditions, and recovering a resulting protein from culture.

In preparing the inventive human PAP, a suitable polynucleotide encoding human PAP, constructed utilizing any of the foregoing techniques is operable linked to an expression vector which is then transformed into a compatible host. Host cells are cultured using conditions appropriate for growth. Expression of the desired human PAP is preferably induced after some predetermined growth level has occurred. Human PAP production is monitored and the desired protein isolated from culture either from a supernatant, or by first lysing host cells with an appropriate agent, or by other methods known to the skilled artisan.

In another preferred embodiment, a polynucleotide encoding human PAP is ligated into a mammalian expression vector. A preferred mammalian expression vector is the plasmid "pCE2." The plasmid pCE2 is derived from pREP7b (Leung, et al., Proc. Natl. Acad. Sci. USA, 92: 4813–4817, 1995) with the RSV promoter region replaced by the CMV enhancer and the elongation factor-1α (EF-1α) promoter and intron. The CMV enhancer of the pCE2 vector is constructed from a 380 bp Xba I-Sph I fragment produced by PCR from pCEP4 (Invitrogen, San Diego, Calif.) using the primers 5'-GGCTCTAGAT ATTAATAGTA ATCAAT-TAC-3' (SEQ ID NO:14) and 5'-CCTCACGCAT GCAC-CATGGT AATAGC-3' (SEQ ID NO:15). The EF-1α promoter and intron (Uetsuki, et al., J. Biol. Chem., 264: 5791–5798, 1989) are constructed from a 1200 bp Sph I-Asp718 I fragment produced by PCR from human genomic DNA using the primers 5'-GGTGCATGCG TGAGGCTCCG GTGC-3' (SEQ ID NO:16) and 5'-GTAGTTTTCA CGGTACCTGA AATGGAAG-3' (SEQ ID NO:17). These 2 fragments are ligated into a Xba I/Asp718 I digested vector derived from pREP7b to generate pCE2.

In another preferred embodiment of the present invention, pCE2 containing a polynucleotide expressing human PAP is used to transform a host cell which then expresses the protein. Preferred host cells include the human embryonic kidney cell line 293-EBNA (Invitrogen, San Diego, Calif.), endothelial ECV304 cells, and epithelial A549 cells.

4. Dephosphorylation of Substrate

In another embodiment, the present invention includes a method of dephosphorylating a substrate by contacting the substrate with an effective amount of isolated human PAP. An "effective amount" of human PAP is an amount which will dephosphorylate a detectable amount of substrate. Such an amount can be determined empirically based on variables well known to those of skill in the art, such as reaction time and temperature.

In one embodiment, the substrate includes phosphatidic acid, lysophosphatidic acid, ceramide 1-phosphate, and sphingosine 1-phosphate. In another embodiment, the isolated human PAP includes PAP-α(1 and 2), PAP-β and PAP-γ and variants thereof.

In a further embodiment, the dephosphorylation of substrate occurs in vitro, by contacting a substrate with recombinantly produced human PAP expressed by the methods described above. The dephosphorylated substrate is then isolated by standard isolation and purification methods, including for example, thin layer chromatography or high pressure liquid chromatography.

In another embodiment, the dephosphorylation of substrate occurs in vivo via the administration of human PAP to a mammal, preferably a human. "Administration" means delivery of human PAP protein to a mammal by methods known to those of skill in the art including, but not limited to: orally, for example in the form of pills, tablets, lacquer tablets, coated tablets, granules, hard gelatin capsules, soft gelatin capsules, solutions, syrups, emulsions, suspensions or aerosol mixtures; rectally, for example in the form of suppositories; parenterally, for example in the form of injection solutions or infusion solutions, microcapsules or rods; percutaneously, for example in the form of ointments or tinctures; transdermally; intravascularly, intracavitarily; intramuscularly; subcutaneously; and nasally, for example in the form of nasal sprays or inhalants.

The administration of human PAP protein includes the administration of the protein combined in a mixture with a pharmaceutically acceptable carrier vehicle. Suitable vehicles and their formulation, inclusive of other human proteins, e.g. human serum albumin, are described for example in Remington's *Pharmaceutical Sciences* by E. W. Martin, which is hereby incorporated by reference. Such compositions will contain an effective amount of protein hereof together with a suitable amount of vehicle in order to prepare pharmaceutically acceptable compositions suitable for effective administration to the host.

Such compositions should be stable for appropriate periods of time, preferably are acceptable for administration to humans and preferably are readily manufacturable. Although pharmaceutical solution formulations are provided in liquid form appropriate for immediate use, formulations may also be provided in frozen or in lyophilized form. In the former case, the composition must be thawed prior to use. The latter form is often used to enhance the stability of the medicinal agent contained in the composition under a wide variety of storage conditions. Such lyophilized preparations are reconstituted prior to use by the addition of suitable pharmaceutically acceptable diluents, such as sterile water or sterile physiological saline solution.

Additionally, administration is meant to include delivery of human PAP protein to a mammal by means of gene therapy techniques, i.e., by the delivery of polynucleotides encoding human PAP to PAP-deficient cells, whereby human PAP is then expressed in the cell. Gene therapy techniques are known to those of skill in the art. For example, listing of present-day vectors suitable for use in gene therapy of the present invention is set forth in Hodgson, *Bio/Technology* 13: 222 (1995). See also, Culver et al., *Science,* 256:1550–62 (1992).

Additionally, liposome-mediated gene transfer is another suitable method for the introduction of a recombinant vector containing a polynucleotide encoding human PAP into a PAP-deficient cell. See Caplen et al., *Nature Med.* 1:39–46 (1995) and Zhu et al., *Science* 261:209–211 (1993).

Additionally, viral vector-mediated gene transfer is also a suitable method for the introduction of a recombinant vector containing the gene encoding human PAP into a PAP-deficient cell. Examples of appropriate viral vectors are adenovirus vectors. Detailed discussions of the use of adenoviral vectors for gene therapy can be found in Berkner, *Biotechniques* 6:616–629 (1988), Trapnell, *Advanced Drug Delivery Rev.* 12:185–199 (1993).

The following examples merely illustrate the invention and, as such, are not to be considered as limiting the invention set forth in the claims.

EXAMPLE 1

Cloning and Expression of Human PAP-α, PAP-β and PAP-γ

Homology search of the Genbank database (Boguski, et al., *Science* 265:1993–1994, 1994) of expressed sequence tag (dbEST) using the murine PAP protein sequence (Kai et al., J. Biol. Chem. 271: 18931–18938, 1996) as probe identified several short stretches of human cDNA sequences with homology to the murine PAP protein sequence. These cDNA sequences of interest were derived from single-run partial sequencing of random human cDNA cloning projects carried out mainly by I.M.A.G.E. Consortium [LLNL] cDNA clones program. Based on the partial DNA sequences available in the GenBank database, the human cDNA clones that are homologous to the murine PAP protein sequence can be grouped into three classes, suggesting the presence of at least three different human PAP variants, designated as PAP-α, PAP-β, and PAP-γ here. For instance, a potential human PAP-α clone (GenBank #H17855) identified contains sequence homologous to aa 272–283 and the 3'-untranslated region of murine PAP; a potential human PAP-β clone (GenBank #W70040) identified contains sequence similarities corresponding to aa 175–251 of murine PAP; and a potential human PAP-γ clone (GenBank #N75714) identified contains sequences similarities corresponding to aa 18–142 of murine PAP. These cDNA clones were purchased (Genome Systems, St. Louis, Mo.) for further analysis. DNA sequence determination of the entire cDNA inserts of these clones showed clone H17855 contained sequences that are homologous to the N- and C-terminal sequences of murine PAP with a gap of about 150 bp that led to a frame shift in reading frame. This clone is most likely a spuriously spliced form of PAP-α clone. Clone W70040 was found to be a full-length PAP-β clone, and clone N75714 was found to be a partial PAP-γ clone with an open reading frame homologous to the region from aa18 to the C-terminus of murine PAP.

To assemble a full-length functional PAP-α clone, synthetic oligonucleotides o_papa1F, 5'-ggcatggtAC CATGTTTGAC AAGACGCGGC-3' (SEQ ID NO:18), based on the N-terminal region of PAP-α and o_papa1R, 5'-CATATGTAGT ATTCAATGTA ACC-3' (SEQ ID NO:19), based on a region downstream of a Pst I site complementary to the coding strand of PAP-α were used to amplify the N-terminal coding region of PAP-α from a human lung cDNA library (Life Technologies, Inc., Gaithersburg, Md.). The 450 bp Acc65 I-Pst I fragment generated was inserted into a Acc65 I/Pst I vector from pBluescript(II)SK(–) (Stratagene, San Diego, Calif.) for further analysis. DNA sequence analysis of the subclones obtained revealed at least two different classes of clones with sequences that diverged at the putative exon of interest, suggesting the presence of two alternatively spliced forms of PAP-α. These two alternatively spliced forms of PAP-α are designated as PAP-α1 and PAP-α2 here. Each of the individual 450 bp Acc65 I-Pst I fragment generated by PCR was combined with the 810 bp Pst I-Not I fragment derived from clone H17855 for ligation into a Acc65 I/Not I mammalian expression vector derived from pCE2 for the generation of expression plasmids for PAP-α1 and PAP-α2. The plasmid pCE2 was derived from pREP7b (Leung, et al., Proc. Natl. Acad. Sci. USA, 92: 4813–4817, 1995) with the RSV promoter region replaced by the CMV enhancer and the elongation factor-1α (EF-1α) promoter and intron. The CMV enhancer of the pCE2 vector was constructed from a 380 bp Xba I-Sph I fragment produced by PCR from pCEP4 (Invitrogen, San Diego, Calif.) using the primers 5'-GGCTCTAGAT ATTAATAGTA ATCAATTAG-3' (SEQ ID NO:14) and 5'-CCTCACGCAT GCACCATGGT AATAGC-3' (SEQ ID NO:15). The EF-1α promoter and intron (Uetsuki, et al., J. Biol. Chem., 264: 5791–5798, 1989) was constructed from a 1200 bp Sph I-Asp718 I fragment produced by PCR from human genomic DNA using the primers 5'-GGTGCATGCG TGAGGCTCCG GTGC-3' (SEQ ID NO:16) and 5'-GTAGTTTTCA CGGTACCTGA AATGGAAG-3' (SEQ ID NO:17). These 2 fragments were ligated into a Xba I/Asp718 I digested vector derived from pREP7b to generate pCE2.

The DNA sequence determined from clone N75714 was used as a probe to search for clones with overlapping sequences in the GenBank database. Clone Z43618 was found to contain an additional 5'-sequence with a potential ATG initiation codon. To assemble a full-length PAP-β clone, synthetic oligonucleotides o_papg1F 5'-tgatggctag cATGCAGAGA AGATGGGTCT TCGTGCTGCT CGACGTG-3' (SEQ ID NO:20), based on the N-terminal region of PAP-γ and o_papg1R, 5'-AGTGCGGGAT CCCAT-AAGTG GTTG-3' (SEQ ID NO:21), based on a region complementary to the coding strand of PAP-γ just downstream of its stop codon were used to generate the full-length coding region of PAP-γ by PCR using the clone N75714 as template. The 820 bp Nhe I-BamH I fragment obtained was then ligated into a Nhe I/BamH I mammalian expression vector derived from pCE2.

FIGS. 1, 2, 3 and 4 show the translated DNA sequences of the putative human cDNA clones for PAP-α1, α2, β and γ, (SEQ ID NOS: 1, 3, 5 and 7) respectively. The designated ATG initiation site for translation of each cDNA clone fulfills the requirement for an adequate initiation site according to Kozak (Kozak, Critical Rev. Biochem. Mol. Biol. 27:385–402, 1992).

The amino acid sequence of each open reading frame (FIGS. 1, 2, 3 and 4 (SEQ ID NOS: 2, 4, 6 and 8)) was used as the query sequence to search for homologous sequences in protein databases. Search of the Genbank database from the National Center for Biotechnology Information (NCBI) using the blastp program showed that these proteins are most homologous to the murine PAP sequence (Kai et al., J. Biol. Chem. 271: 18931–18938, 1996), and a rat endoplasmic reticulum resident transmembrane protein of unknown function, *Dri* 42, whose expression is up-regulated during epithelial differentiation (Barila et al., J. Biol. Chem. 271: 29928–29936, 1996).

EXAMPLE 2

Activati n of PAP-β Transcripti n by IL1-β

It is possible that activation of PAP-β expression can counter-balance the inflammatory response from IL-1β stimulation through degradation of the excess amount of PA in cells. To determine whether IL1-β, an inflammatory cytokine, would activate the transcription of PAP mRNAs, Northern analysis of PAP-β mRNA levels (FIG. 6) was performed in human endothelial ECV304 cells at various times after IL-1β stimulation. FIG. 6 shows that PAP-β mRNA expression was induced after incubation of ECV304 cells with IL-1β after at least 6 hours, suggesting that PAP-β is a late-response gene to IL-1β stimulation. This indicates that human PAP may act to reduce IL-1 β induced inflammation by degrading excess PA in cells.

EXAMPLE 3

PAP-α1 and PAP-α2 Dephosphorylation of PA to DAG

Figure 7:
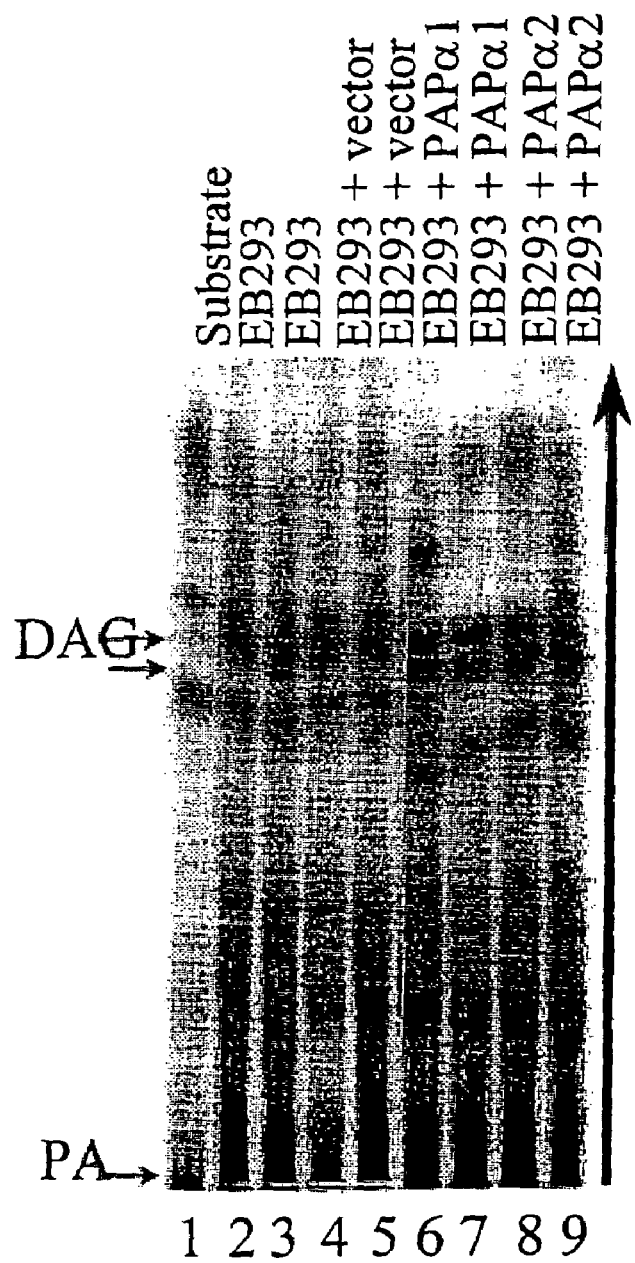
FIG. 7 depicts a thin layer chromatography analysis demonstrating the increase in PA dephosphorylation in cells transfected with either the PAP-α1 or PAP-α2 cDNA expression plasmids.

The expression of PAP-α1 and PAP-α2 cDNA was found to increase PA dephosphorylation in mammalian cells. The expression plasmids for PAP-α1, PAP-α2 and the control vector were transiently transfected into 293-EBNA (EB293) cells (Invitrogen, San Diego, Calif.) using the lipofectant DOTAP (Boehringer Mannheim, Indianapolis, Ind.). PAP activities were followed by TLC analysis based on the conversion of $[C^{14}]$PA (DuPont NEN, Boston, Mass.) to $[C^{14}]$DAG using membrane fractions isolated from the various cell extracts. FIG. 7 shows membrane fractions derived from cells transfected with either the PAP-α1 (lanes 6 and 7) or PAP-α2 (lanes 8 and 9) produced more $[C^{14}]$DAG those from untransfected cells (lanes 2 and 3) or from cells transfected with the control pCE2 vector (lanes 4 and 5). In this particular chromatography system, DAG can be resolved into two bands, possibly due to heterogeneity in the acyl-chains. It appears that PAP-α1 and PAP-α2 preferentially dephosphorylate different species of PA as evidenced by the change in relative intensity of the two DAG bands (lanes 6 to 9).

EXAMPLE 4

Differential Expression of PAP-α mRNA in Selected Tumor Versus Normal Tissues

Figure 8:
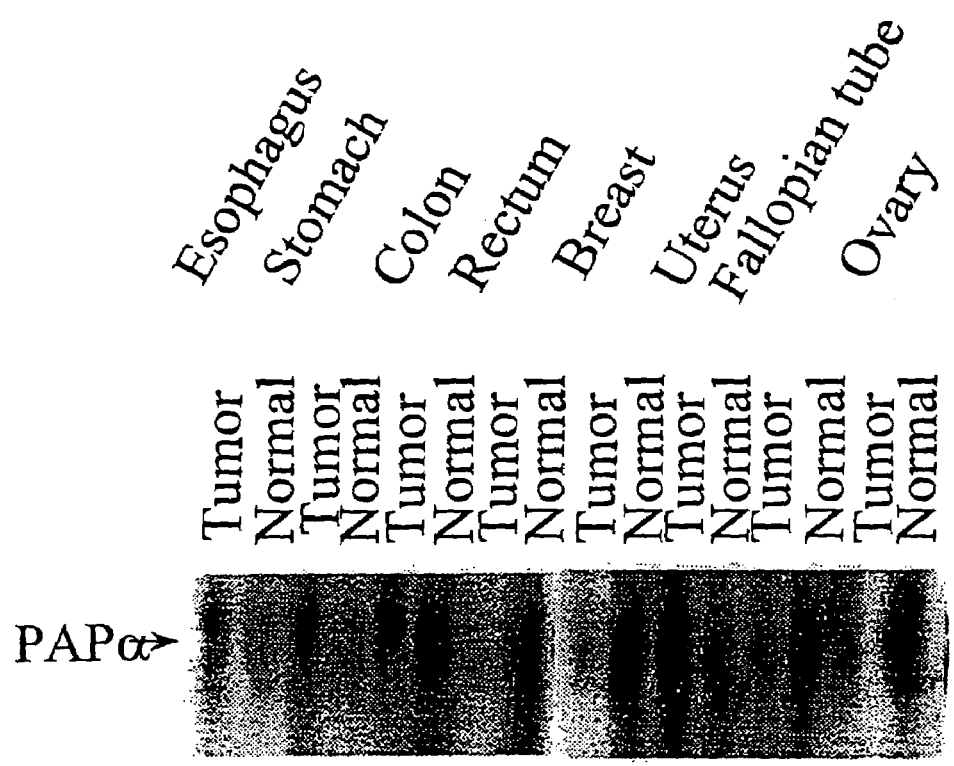
FIG. 8 shows the differential expression of PAP-α mRNA in various tumor versus normal tissues.
Figure 9:
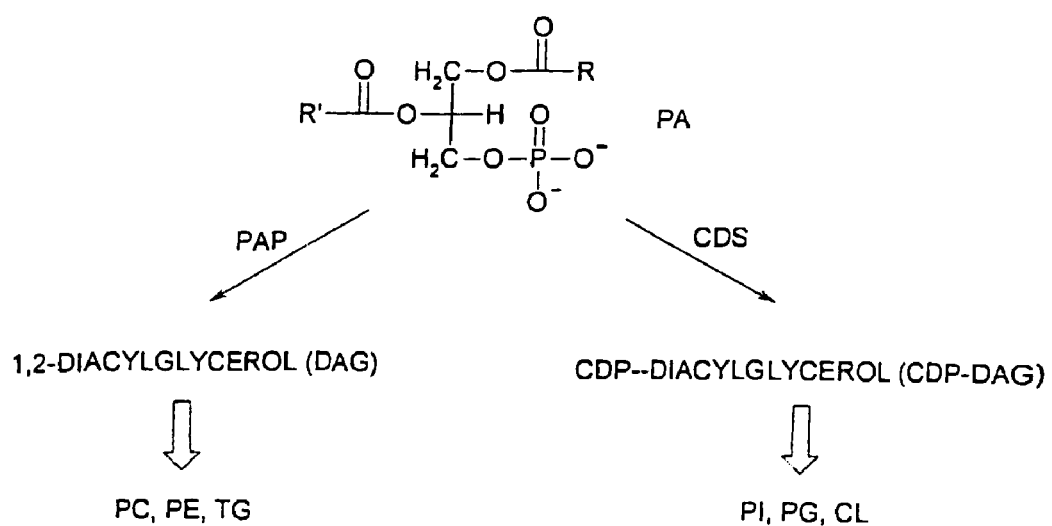
FIG. 9 is a schematic representation of glycerophospholipid biosynthesis involving the conversion of PA to either DAG or CDP-DAG. The synthesis of PA to DAG involves the PAP enzyme, while the synthesis of PA to CPD-DAG involves the CDS enzyme.

The possibility that PAP-α expression can degrade the excess amount of PA in cells suggests that PAP-α may be down-regulated in tumor cells when compared to normal cells, as tumor cells tend to be more inflammatory due to a possibly higher level of PA when compared to normal or resting cells. To test this hypothesis, Northern analysis using PAP-α(1 and 2) cDNA probe was performed on RNA blots derived from various matching pairs of tumor and normal tissues (Invitrogen, Carlsbad, Calif.). FIG. 8 shows the expression levels of PAP-α mRNA are substantially higher in five out of eight of the normal tissues examined; namely, colon, rectal, breast, fallopian tube, and ovarian tissues when compared to the corresponding tumor tissues.

What is claimed is:

1. An isolated human phosphatidic acid phosphatase protein, wherein said protein comprises a polypeptide sequence selected from the group consisting of (i) the sequence at amino acid number 1 to amino acid number 284 in FIG. 1 (SEQ ID NO:2), (ii) the sequence at amino acid number 1 to amino acid number 285 in FIG. 2 (SEQ ID NO:4), and (iii) the sequence at amino acid number 1 to amino acid number 276 in FIG. 4 (SEQ ID NO:8).

2. A isolated and purified polynucleotide encoding a polypeptide comprising the amino acid sequence of SEQ ID NO:2.

3. An isolated polynucleotide encoding human phosphatidic acid phosphatase, wherein said polynucleotide encodes a protein comprising a polypeptide sequence selected from the group consisting of (i) the sequence at amino acid number 1 to amino acid number 285 in FIG. 2 (SEQ ID NO:4), and (ii) the sequence at amino acid number 1 to amino acid number 276 in FIG. 4 (SEQ ID NO:8).

4. A method of preparing a human phosphatidic acid phosphatase protein comprising the steps of (i) transforming a host cell with an expression vector comprising a polynucleotide encoding human phosphatidic acid phosphatase, (ii) culturing said transformed host cells which express said protein and (iii) isolating said protein, wherein said polynucleotide encoding human phosphatidic acid comprises a polynucleotide encoding a polypeptide sequence selected from the group consisting of (a) amino acids 1–284 of FIG. 1 (SEQ ID NO: 2), (b) amino acids 1–285 of FIG. 2 (SEQ ID NO: 4), (c) amino acids 1–311 of FIG. 3 (SEQ ID NO: 6), and (d) amino acids 1–276 of FIG. 4 (SEQ ID NO: 8).

5. A method of dephosphorylating a substrate comprising recombinantly producing a human phosphatidic acid phosphatase protein and contacting said substrate with an effective amount of said recombinantly produced human phosphatidic acid phosphatase protein such that said protein catalyzes the dephosphorylation of said substrate, where said protein comprises a polypeptide sequence selected from the group consisting of (a) amino acids 1–284 of FIG. 1 (SEQ ID NO: 2), (b) amino acids 1–285 of FIG. 2 (SEQ ID NO: 4), (c) amino acids 1–311 of FIG. 3 (SEQ ID NO: 6), and (d) amino acids 1–276 of FIG. 4 (SEQ ID NO: 8).

6. The method of claim 5, wherein said substrate is selected from the group consisting of phosphatidic acid, lysophosphatidic acid, ceramide 1-phosphate, and sphingosine 1-phosphate.

7. The method of claim 5, wherein said contacting is effected in vitro, and further comprises the step of isolating said dephosphoryled substrate.

8. The method of claim 5, wherein said contacting step occurs in vivo and is effected by the administration of said human phosphatidic acid phosphatase to a mammal in need thereof.

* * * * *